(12) United States Patent
Tokunaga et al.

(10) Patent No.: US 11,123,463 B2
(45) Date of Patent: Sep. 21, 2021

(54) BLOOD PURIFICATION APPARATUS

(71) Applicant: Nikkiso Company Limited, Tokyo (JP)

(72) Inventors: Makoto Tokunaga, Shizuoka (JP); Kunihiko Akita, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 401 days.

(21) Appl. No.: 15/850,943

(22) Filed: Dec. 21, 2017

(65) Prior Publication Data

US 2018/0133384 A1 May 17, 2018

Related U.S. Application Data

(63) Continuation of application No. PCT/JP2016/068786, filed on Jun. 24, 2016.

(30) Foreign Application Priority Data

Jun. 24, 2015 (JP) .............................. JP2015-126900

(51) Int. Cl.
*A61M 1/16* (2006.01)
*A61M 1/36* (2006.01)
(Continued)

(52) U.S. Cl.
CPC .......... *A61M 1/1603* (2014.02); *A61M 1/267* (2014.02); *A61M 1/3639* (2013.01);
(Continued)

(58) Field of Classification Search
CPC .. A61M 1/1603; A61M 1/276; A61M 1/3621; A61M 1/1006; A61M 1/3626;
(Continued)

(56) References Cited

U.S. PATENT DOCUMENTS

| 3,046,788 A | 7/1962 | Laimins |
|---|---|---|
| 4,090,404 A | 5/1978 | Dupont |

(Continued)

FOREIGN PATENT DOCUMENTS

| EP | 1666078 | 6/2006 |
|---|---|---|
| EP | 2361643 A1 | 8/2011 |

(Continued)

OTHER PUBLICATIONS

Extended European Search Report dated Feb. 1, 2019, Application No. 16814474.9.

(Continued)

*Primary Examiner* — Tatyana Zalukaeva
*Assistant Examiner* — Heather K Barnwell
(74) *Attorney, Agent, or Firm* — Young Basile Hanlon & MacFarlane, P.C.

(57) ABSTRACT

A blood purification apparatus in which the error in the amount of discharge from a blood pump that is caused by the change in the suction pressure of the blood pump is reduced. A blood purification apparatus includes a blood circuit through which blood of a patient is extracorporeally circulated; a dialyzer connected to proximal ends of an arterial blood circuit and a venous blood circuit and that purifies the blood extracorporeally circulating through the blood circuit; a squeezable tube connected to the arterial blood circuit; a blood pump allowing liquid in the squeezable tube to flow by squeezing the squeezable tube in a lengthwise direction while compressing the squeezable tube in a radial direction; and a pressure-detecting device attached to a predetermined position of the arterial blood circuit that is nearer to a distal end than a position where the blood pump is provided, the pressure-detecting device being capable of detecting a suction pressure of the blood pump.

20 Claims, 23 Drawing Sheets

(51) Int. Cl.
*A61M 1/26* (2006.01)
*A61M 60/50* (2021.01)
*A61M 60/113* (2021.01)
*A61M 60/279* (2021.01)
*A61M 60/892* (2021.01)
*A61M 60/894* (2021.01)

(52) U.S. Cl.
CPC ......... *A61M 1/3626* (2013.01); *A61M 1/3638* (2014.02); *A61M 60/113* (2021.01); *A61M 60/279* (2021.01); *A61M 60/50* (2021.01); *A61M 60/892* (2021.01); *A61M 60/894* (2021.01); *A61M 2205/3317* (2013.01); *A61M 2205/3331* (2013.01); *A61M 2205/3334* (2013.01); *A61M 2205/3337* (2013.01); *A61M 2205/3365* (2013.01); *A61M 2205/3375* (2013.01)

(58) Field of Classification Search
CPC .............. A61M 1/3639; A61M 1/1086; A61M 1/1096; A61M 1/1087; A61M 1/3638; A61M 1/1093; A61M 2205; A61M 1/3334; A61M 1/3317; A61M 1/3331; A61M 1/3337; A61M 1/3365; A61M 1/3375
See application file for complete search history.

(56) References Cited

U.S. PATENT DOCUMENTS

| | | | |
|---|---|---|---|
| 4,460,355 A | 7/1984 | Layman | |
| 4,498,843 A * | 2/1985 | Schneider | A61M 5/14232 222/14 |
| 4,534,756 A | 8/1985 | Nelson | |
| 4,743,228 A | 5/1988 | Butterfield | |
| 4,762,518 A | 8/1988 | Kreinick | |
| 4,784,576 A | 11/1988 | Bloom | |
| 4,969,808 A | 11/1990 | Tsukada | |
| 5,024,099 A | 6/1991 | Lee | |
| 5,215,450 A | 6/1993 | Tamari | |
| 5,336,051 A | 8/1994 | Tamari | |
| 5,356,378 A | 10/1994 | Doan | |
| 5,380,172 A | 1/1995 | Ulbing | |
| 5,429,783 A | 7/1995 | Tamari | |
| 5,720,721 A | 2/1998 | Dumas et al. | |
| 5,813,842 A | 9/1998 | Tamari | |
| 5,814,004 A | 9/1998 | Tamari | |
| 5,920,054 A | 7/1999 | Uber | |
| 5,927,951 A | 7/1999 | Tamari | |
| 6,039,078 A | 3/2000 | Tamari | |
| 6,044,691 A | 4/2000 | Kenley et al. | |
| 6,374,084 B1 | 4/2002 | Fok | |
| 6,497,680 B1 | 12/2002 | Holst | |
| 6,868,720 B2 | 3/2005 | Lobdell | |
| 7,004,924 B1 | 2/2006 | Brugger | |
| 7,037,092 B2 | 5/2006 | Kagawa | |
| 7,147,616 B2 | 12/2006 | Pedrazzi et al. | |
| 7,462,163 B2 | 12/2008 | Yap | |
| 7,935,912 B2 | 5/2011 | Arima | |
| 8,011,905 B2 | 9/2011 | Artsyukhovich | |
| 9,004,886 B2 | 4/2015 | Beck | |
| 9,192,708 B2 | 11/2015 | Iwahori et al. | |
| 9,662,433 B2 | 5/2017 | Matsuo et al. | |
| 2001/0004444 A1 | 6/2001 | Baser | |
| 2002/0151838 A1 | 10/2002 | Beck et al. | |
| 2003/0040700 A1 | 2/2003 | Hickle et al. | |
| 2003/0214412 A1 | 11/2003 | Ho | |
| 2005/0043665 A1 * | 2/2005 | Vinci | A61M 1/1086 604/5.01 |
| 2006/0079826 A1 | 4/2006 | Beden et al. | |
| 2007/0217933 A1 | 9/2007 | Haser et al. | |
| 2008/0154095 A1 | 6/2008 | Stubkjaer | |
| 2009/0024070 A1 | 1/2009 | Gelfand et al. | |
| 2009/0043240 A1 | 2/2009 | Robinson et al. | |
| 2009/0137941 A1 * | 5/2009 | Lynch | A61M 1/363 604/6.11 |
| 2009/0312686 A1 | 12/2009 | Sakamoto et al. | |
| 2010/0049134 A1 | 2/2010 | Schuman, Jr. | |
| 2010/0106466 A1 | 4/2010 | Frohlich | |
| 2010/0168640 A1 | 7/2010 | Kopperschmidt et al. | |
| 2010/0179467 A1 | 7/2010 | Günther et al. | |
| 2010/0203179 A1 | 8/2010 | Kaushik | |
| 2010/0274172 A1 | 10/2010 | Guenther et al. | |
| 2011/0130741 A1 | 6/2011 | Miles et al. | |
| 2011/0139690 A1 | 6/2011 | Akita et al. | |
| 2011/0213289 A1 | 9/2011 | Toyoda | |
| 2011/0230814 A1 | 9/2011 | Kopperschmidt et al. | |
| 2012/0000547 A1 | 1/2012 | Gronau et al. | |
| 2012/0082576 A1 | 4/2012 | Beck | |
| 2012/0150089 A1 | 6/2012 | Penka et al. | |
| 2013/0023812 A1 * | 1/2013 | Hasegawa | A61M 1/1613 604/6.09 |
| 2013/0035626 A1 | 2/2013 | Suzuki | |
| 2013/0150766 A1 | 6/2013 | Gambro | |
| 2013/0172803 A1 | 7/2013 | Gambro | |
| 2013/0292313 A1 | 11/2013 | Fava et al. | |
| 2014/0138301 A1 | 5/2014 | Iwahori et al. | |
| 2014/0219829 A1 | 8/2014 | Matsuo et al. | |
| 2015/0021244 A1 | 1/2015 | Furuhashi et al. | |
| 2015/0150136 A1 | 6/2015 | Furuhashi et al. | |
| 2015/0217040 A1 | 8/2015 | Matsuo et al. | |
| 2015/0238677 A1 * | 8/2015 | Akita | F04B 43/1253 417/63 |
| 2016/0250405 A1 | 9/2016 | Kogoshi et al. | |
| 2017/0028117 A1 | 2/2017 | Mochizuki | |
| 2017/0095602 A1 | 4/2017 | Ishizaki et al. | |
| 2017/0173249 A1 | 6/2017 | Matshushita et al. | |
| 2017/0312412 A1 | 11/2017 | Mochizuki et al. | |

FOREIGN PATENT DOCUMENTS

| | | |
|---|---|---|
| EP | 2535067 A1 | 12/2012 |
| EP | 2749858 | 7/2014 |
| EP | 2883558 A1 | 6/2015 |
| JP | S56-113083 A | 9/1981 |
| JP | S60-153138 | 10/1985 |
| JP | S64-022357 | 2/1989 |
| JP | H03-001290 | 1/1991 |
| JP | H03-073162 A | 3/1991 |
| JP | H04-015938 | 2/1992 |
| JP | H06-047090 | 2/1994 |
| JP | H08-510812 A | 11/1996 |
| JP | 2003-093501 A | 4/2003 |
| JP | 2003-093503 | 4/2003 |
| JP | 2003-519539 | 6/2003 |
| JP | 2003-265601 | 9/2003 |
| JP | 2003-290342 | 10/2003 |
| JP | 2004-016619 A | 1/2004 |
| JP | 2004-049494 | 2/2004 |
| JP | 2004-187990 | 7/2004 |
| JP | 2004-313522 A | 11/2004 |
| JP | 2005-503202 A | 2/2005 |
| JP | 2005-253555 A | 9/2005 |
| JP | 2006-280775 A | 10/2006 |
| JP | 2007-007435 A | 1/2007 |
| JP | 3128724 U | 1/2007 |
| JP | 2007-020962 | 2/2007 |
| JP | 2007-135885 | 6/2007 |
| JP | 2007-167108 A | 7/2007 |
| JP | 2007-224909 A | 9/2007 |
| JP | 2007-282737 A | 11/2007 |
| JP | 2008-000425 A | 1/2008 |
| JP | 2008-002388 A | 1/2008 |
| JP | 2008-208808 | 9/2008 |
| JP | 2008-289635 A | 12/2008 |
| JP | 2009-112651 A | 5/2009 |
| JP | 2009-131412 A | 6/2009 |
| JP | 2009-525770 | 7/2009 |
| JP | 2009-207706 A | 9/2009 |
| JP | 2010-000161 A | 1/2010 |
| JP | 2010-099484 | 5/2010 |
| JP | 2010-136841 | 6/2010 |

(56) References Cited

FOREIGN PATENT DOCUMENTS

| | | |
|---|---|---|
| JP | 2010-184029 A | 8/2010 |
| JP | 2010-188170 A | 9/2010 |
| JP | 2010-190062 A | 9/2010 |
| JP | 2010-273693 A | 12/2010 |
| JP | 2010-273784 A | 12/2010 |
| JP | 2011-030880 A | 2/2011 |
| JP | 2011-161060 A | 8/2011 |
| JP | 2011-200407 | 10/2011 |
| JP | 2011-239860 | 12/2011 |
| JP | 2012-095842 | 5/2012 |
| JP | 2012-095843 A | 5/2012 |
| JP | 2012-139405 A | 7/2012 |
| JP | 2012-192099 A | 10/2012 |
| JP | 2012-192100 A | 10/2012 |
| JP | 2013-027494 A | 2/2013 |
| JP | 2013-027495 A | 2/2013 |
| JP | 2013-056079 A | 3/2013 |
| JP | 2014-083092 | 5/2014 |
| JP | 2014-097197 A | 5/2014 |
| JP | 2014083092 A * 5/2014 .......... F04B 43/1253 | |
| JP | 2014-101770 | 6/2014 |
| JP | 2014-184108 | 10/2014 |
| WO | 1994/028309 | 8/1994 |
| WO | 1995/010310 A1 | 4/1995 |
| WO | 1997/010013 | 3/1997 |
| WO | 2001/051106 | 7/2001 |
| WO | 2004/000391 | 12/2003 |
| WO | 2005/118485 A | 12/2005 |
| WO | 2007/093064 A1 | 8/2007 |
| WO | 2009/004777 | 1/2009 |
| WO | 2009/074588 A1 | 6/2009 |
| WO | 2010/020380 A1 | 2/2010 |
| WO | 2011-099521 A1 | 8/2011 |
| WO | 2012/017959 A1 | 2/2012 |
| WO | 2013/031965 A1 | 3/2013 |
| WO | 2013/151114 A1 | 10/2013 |
| WO | 2014/024972 A1 | 2/2014 |
| WO | 2014/107656 A1 | 7/2014 |
| WO | 2015/068833 A1 | 5/2015 |

OTHER PUBLICATIONS

International Search Report from the Japanese Patent Office for Application No. PCT/JP2016/068786 dated Aug. 2, 2016.
Co-Pending U.S. Appl. No. 14/688,064, filed Apr. 16, 2015, also published as US 2015/0217040 on Aug. 6, 2015.
Co-Pending U.S. Appl. No. 14/688,068, filed Apr. 16, 2015, also published as US 2015/0238677 on Aug. 27, 2015.
Co-Pending U.S. Appl. No. 15/292,404, filed Oct. 13, 2016, also published as US 2017/0028117 on Feb. 2, 2017.
Co-Pending U.S. Appl. No. 15/387,913, filed Dec. 22, 2016 also published as US 2017/0095602 on Apr. 6, 2017.
Co-Pending U.S. Appl. No. 15/819,219, filed Nov. 21, 2017.

* cited by examiner

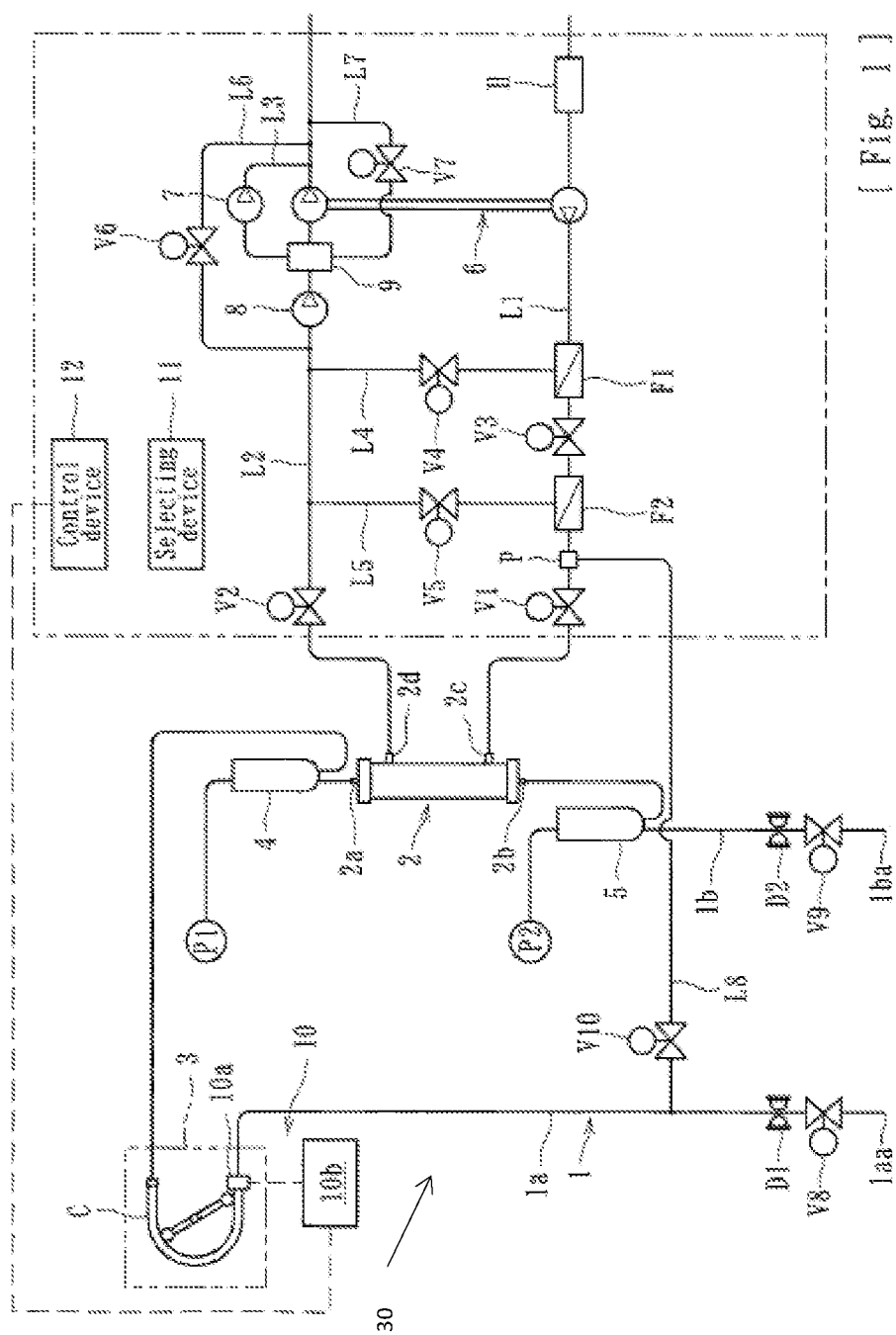
[Fig. 1]

[Fig. 2]
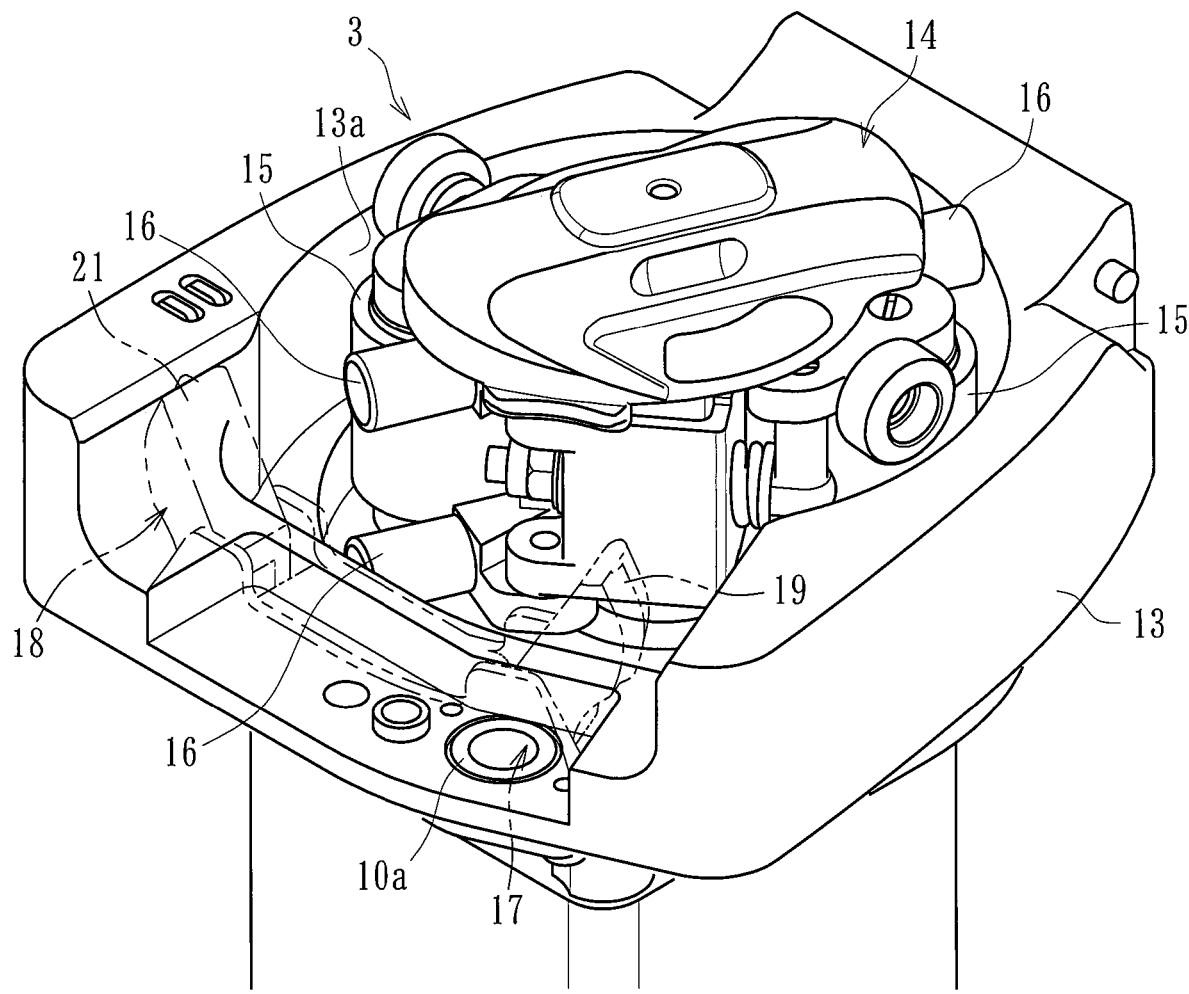

[ Fig. 3 ]
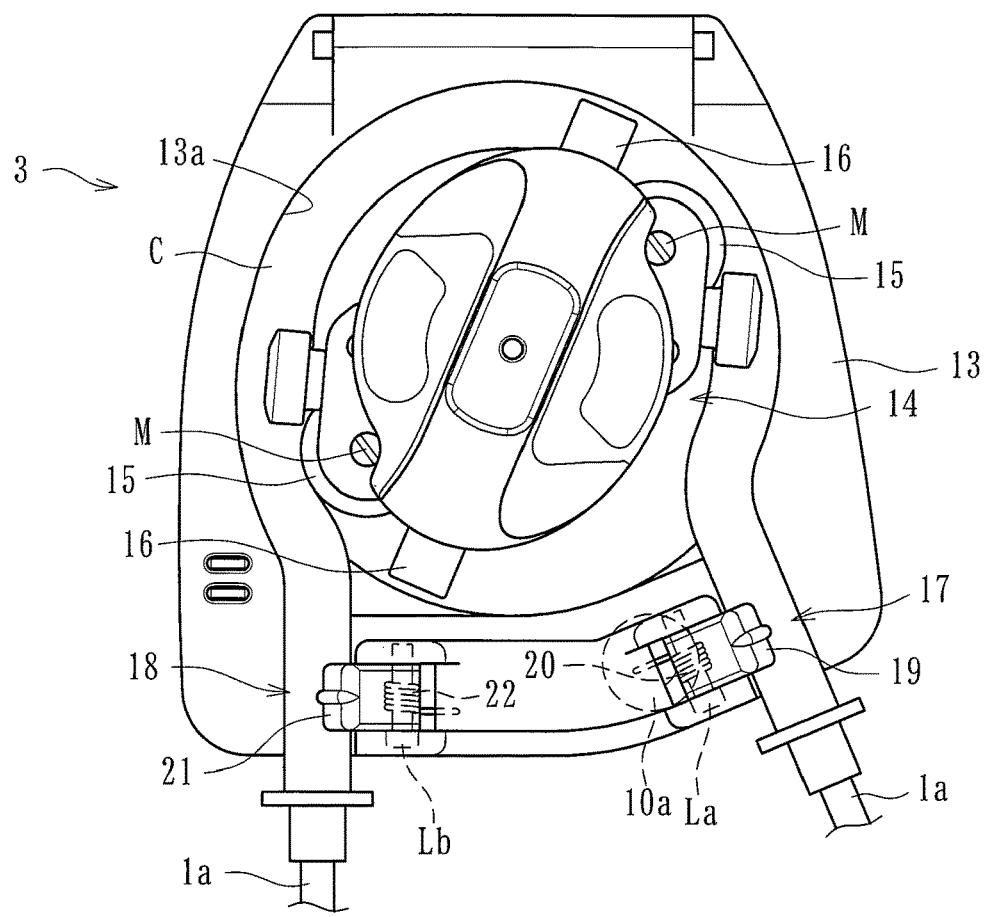
[ Fig. 4 ]
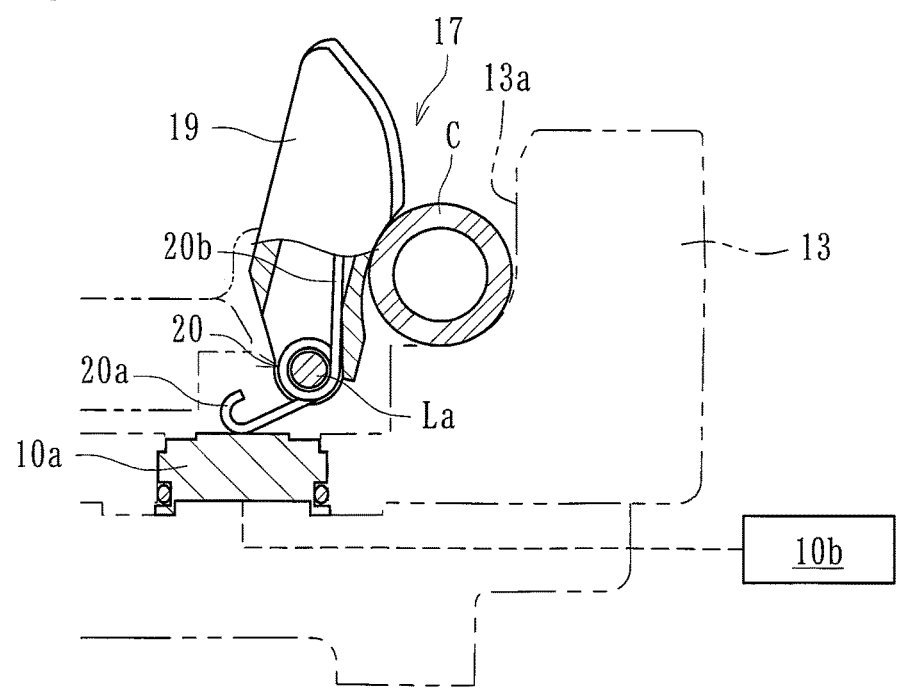

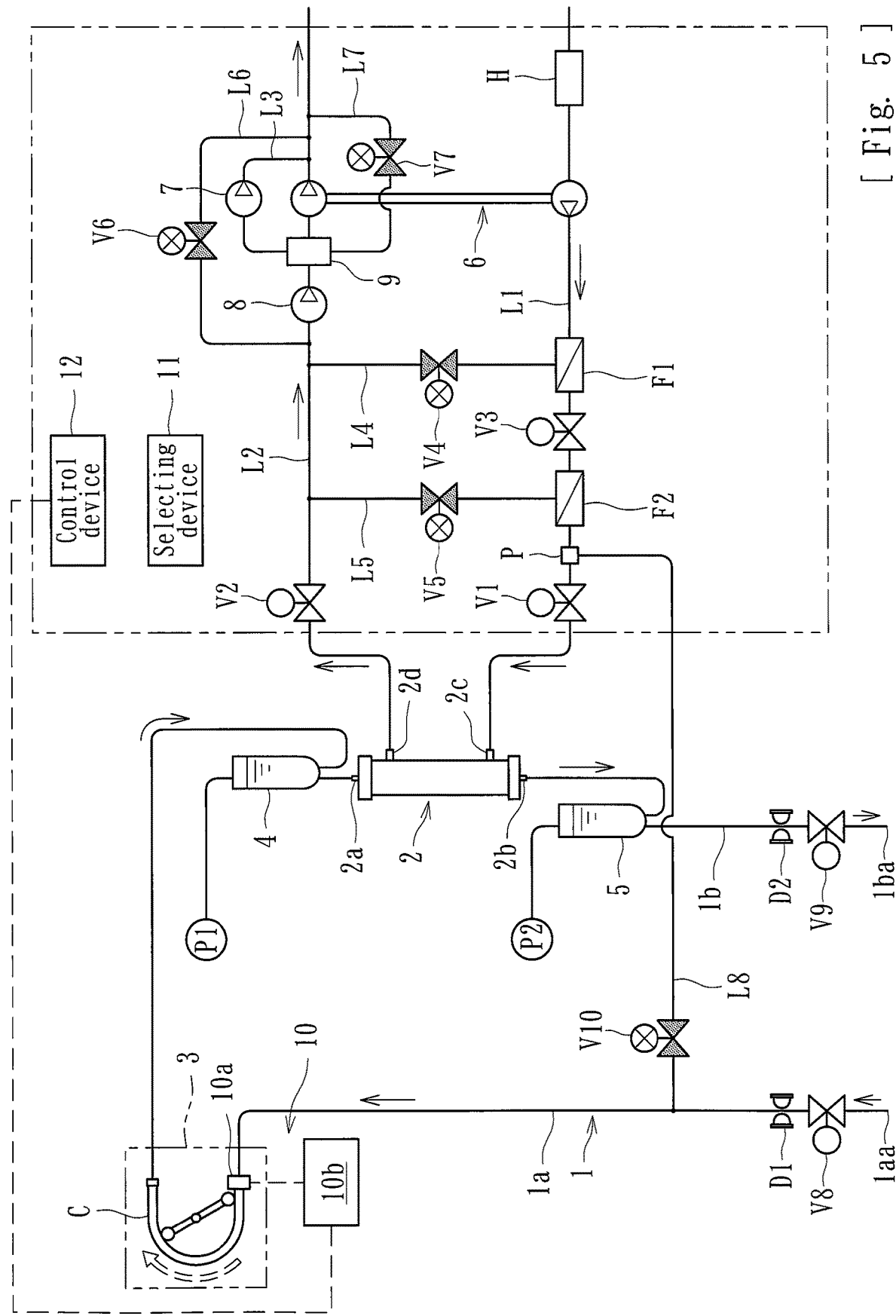
[Fig. 5]

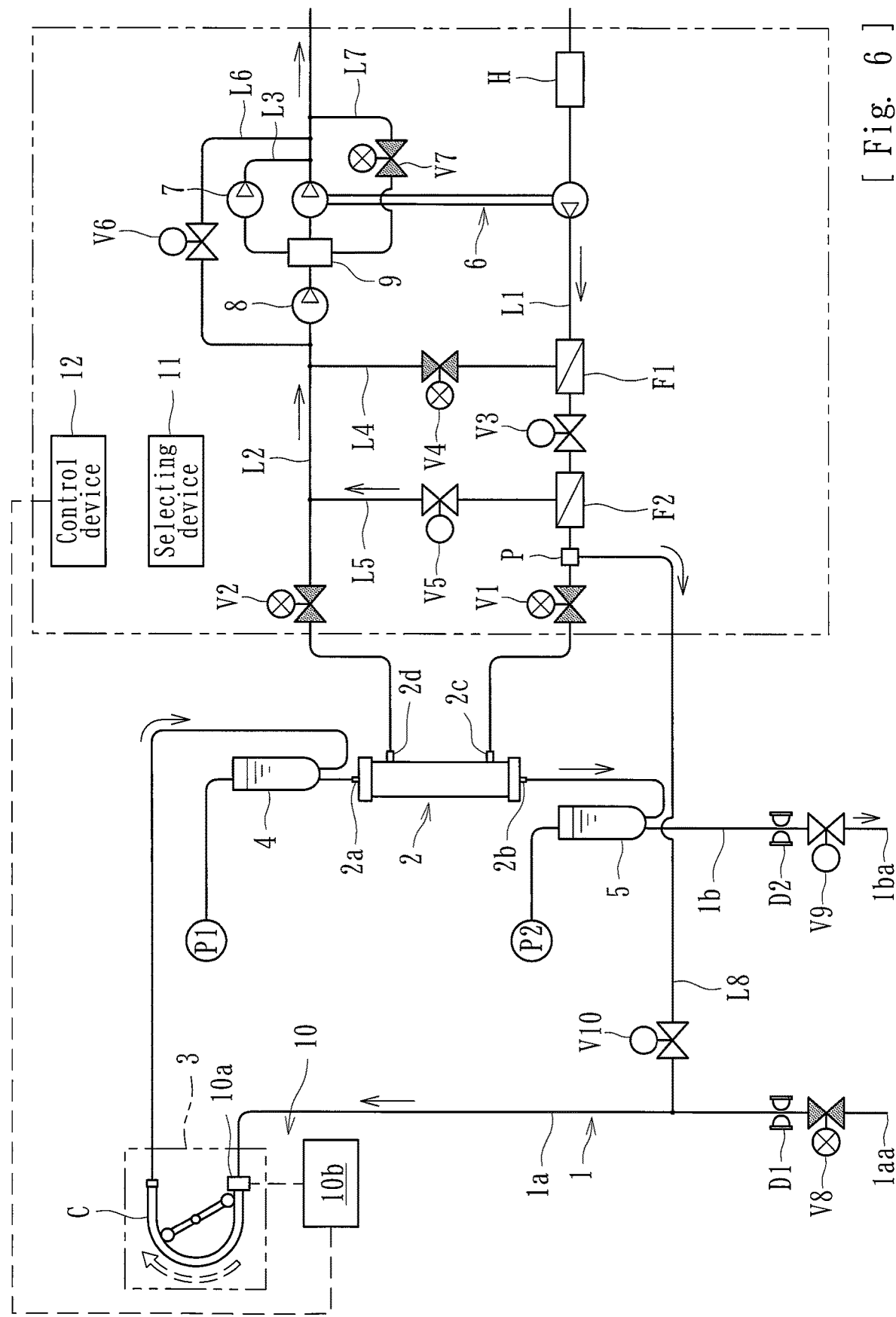
[ Fig. 6 ]

[ Fig. 7 ]
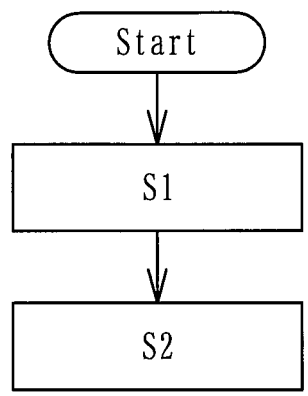
S1:Make settings for suction pressure = Predetermined value
S2:Correct driving speed of blood pump

[Fig. 8]

| Sample | Small diameter (0mmHg) | | | | | | | |
|---|---|---|---|---|---|---|---|---|
| | Inside Diameter | Outside Diameter | Material | suction pressure | Preset flow rate [ml/min] | Actual flow rate [ml/min] | Error [%] | Amount of discharge at 10%-reduced speed (estimation) [ml/min] | Error [%] |
| 1 | 6.45 | 9.55 | ME6002 | 0 | 40 | 42.5 | 6.3 | 38.25 | -4.4 |
| 2 | 6.45 | 9.55 | T-H8D | 0 | 40 | 42.5 | 6.3 | 38.25 | -4.4 |
| 3 | 6.6 | 9.7 | ME6002 | 0 | 40 | 44 | 10.0 | 39.60 | -1.0 |
| 4 | 6.6 | 9.7 | T-H8D | 0 | 40 | 44.75 | 11.9 | 40.28 | 0.7 |
| 5 | 6.75 | 9.85 | ME6002 | 0 | 40 | 45.5 | 13.8 | 40.95 | 2.4 |
| 6 | 6.75 | 9.85 | T-H8D | 0 | 40 | 45 | 12.5 | 40.50 | 1.3 |
| 1 | 6.45 | 9.55 | ME6002 | 0 | 200 | 208.75 | 4.4 | 187.88 | -6.1 |
| 2 | 6.45 | 9.55 | T-H8D | 0 | 200 | 210.25 | 5.1 | 189.23 | -5.4 |
| 3 | 6.6 | 9.7 | ME6002 | 0 | 200 | 217.75 | 8.9 | 195.98 | -2.0 |
| 4 | 6.6 | 9.7 | T-H8D | 0 | 200 | 220.5 | 10.3 | 198.45 | -0.8 |
| 5 | 6.75 | 9.85 | ME6002 | 0 | 200 | 225 | 12.5 | 202.50 | 1.3 |
| 6 | 6.75 | 9.85 | T-H8D | 0 | 200 | 224 | 12.0 | 201.60 | 0.8 |
| 1 | 6.45 | 9.55 | ME6002 | 0 | 350 | 367.25 | 4.9 | 330.53 | -5.6 |
| 2 | 6.45 | 9.55 | T-H8D | 0 | 350 | 369.25 | 5.5 | 332.33 | -5.1 |
| 3 | 6.6 | 9.7 | ME6002 | 0 | 350 | 382.25 | 9.2 | 344.03 | -1.7 |
| 4 | 6.6 | 9.7 | T-H8D | 0 | 350 | 385.75 | 10.2 | 347.18 | -0.8 |
| 5 | 6.75 | 9.85 | ME6002 | 0 | 350 | 397.75 | 13.6 | 357.98 | 2.3 |
| 6 | 6.75 | 9.85 | T-H8D | 0 | 350 | 392 | 12.0 | 352.80 | 0.8 |

[Fig. 9]
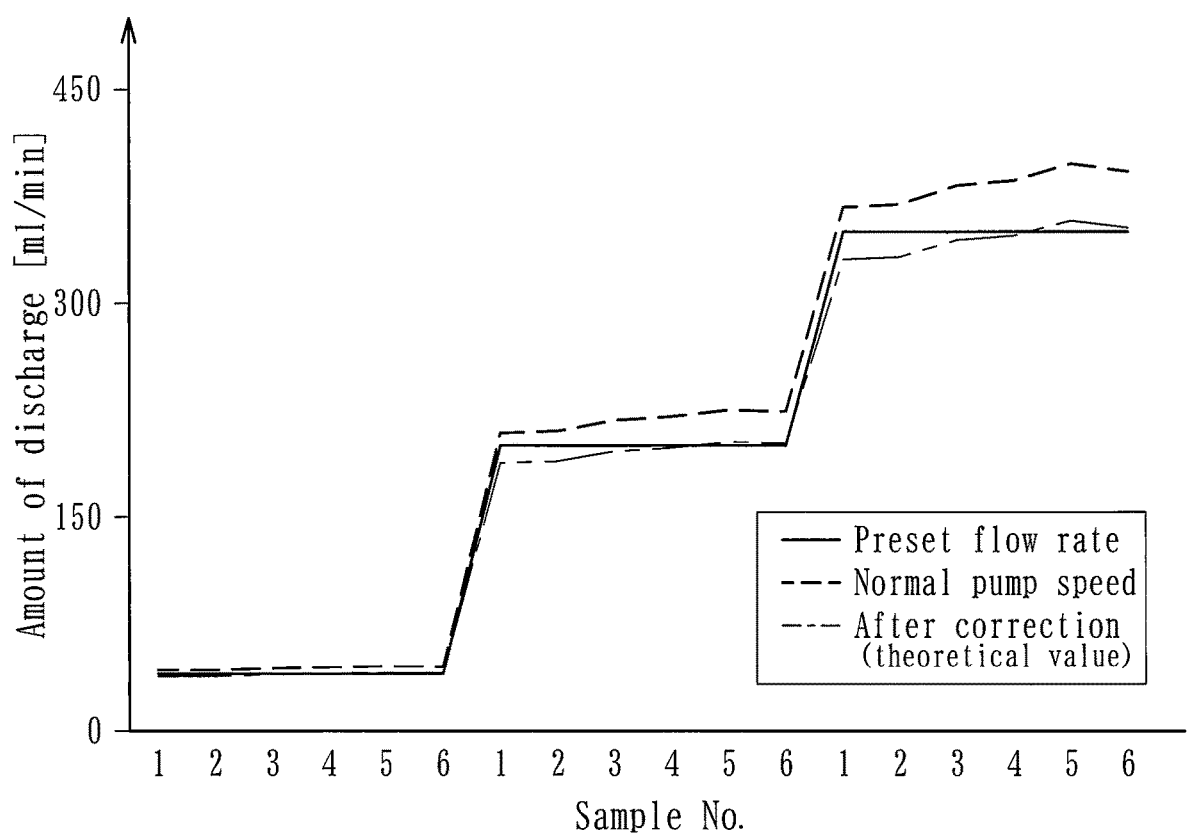

[Fig. 10]

| Sample | Inside Diameter | Outside Diameter | Material | suction pressure | Large diameter (0mmHg) | | | | |
|---|---|---|---|---|---|---|---|---|---|
| | | | | | Preset flow rate [ml/min] | Actual flow rate [ml/min] | Error [%] | Amount of discharge at 5%-reduced speed (estimation) [ml/min] | Error [%] |
| 1 | 7.85 | 12.1 | ME6002 | 0 | 40 | 40 | 0.0 | 38.00 | -5.0 |
| 2 | 7.85 | 12.1 | T-H8D | 0 | 40 | 40.75 | 1.9 | 38.71 | -3.2 |
| 3 | 8 | 12.2 | ME6002 | 0 | 40 | 41.5 | 3.8 | 39.43 | -1.4 |
| 4 | 8 | 12.2 | T-H8D | 0 | 40 | 42 | 5.0 | 39.90 | -0.3 |
| 5 | 8.15 | 12.4 | ME6002 | 0 | 40 | 43.5 | 8.8 | 41.33 | 3.3 |
| 6 | 8.15 | 12.4 | T-H8D | 0 | 40 | 42.5 | 6.3 | 40.38 | 0.9 |
| 1 | 7.85 | 12.1 | ME6002 | 0 | 200 | 200 | 0.0 | 190.00 | -5.0 |
| 2 | 7.85 | 12.1 | T-H8D | 0 | 200 | 202 | 1.0 | 191.90 | -4.1 |
| 3 | 8 | 12.2 | ME6002 | 0 | 200 | 206 | 3.0 | 195.70 | -2.2 |
| 4 | 8 | 12.2 | T-H8D | 0 | 200 | 208.5 | 4.3 | 198.08 | -1.0 |
| 5 | 8.15 | 12.4 | ME6002 | 0 | 200 | 215.75 | 7.9 | 204.96 | 2.5 |
| 6 | 8.15 | 12.4 | T-H8D | 0 | 200 | 210.5 | 5.3 | 199.98 | 0.0 |
| 1 | 7.85 | 12.1 | ME6002 | 0 | 600 | 603.5 | 0.6 | 573.33 | -4.4 |
| 2 | 7.85 | 12.1 | T-H8D | 0 | 600 | 607 | 1.2 | 576.65 | -3.9 |
| 3 | 8 | 12.2 | ME6002 | 0 | 600 | 630 | 5.0 | 598.50 | -0.3 |
| 4 | 8 | 12.2 | T-H8D | 0 | 600 | 634 | 5.7 | 602.30 | 0.4 |
| 5 | 8.15 | 12.4 | ME6002 | 0 | 600 | 657 | 9.5 | 624.15 | 4.0 |
| 6 | 8.15 | 12.4 | T-H8D | 0 | 600 | 643 | 7.2 | 610.85 | 1.8 |

[ Fig. 11 ]
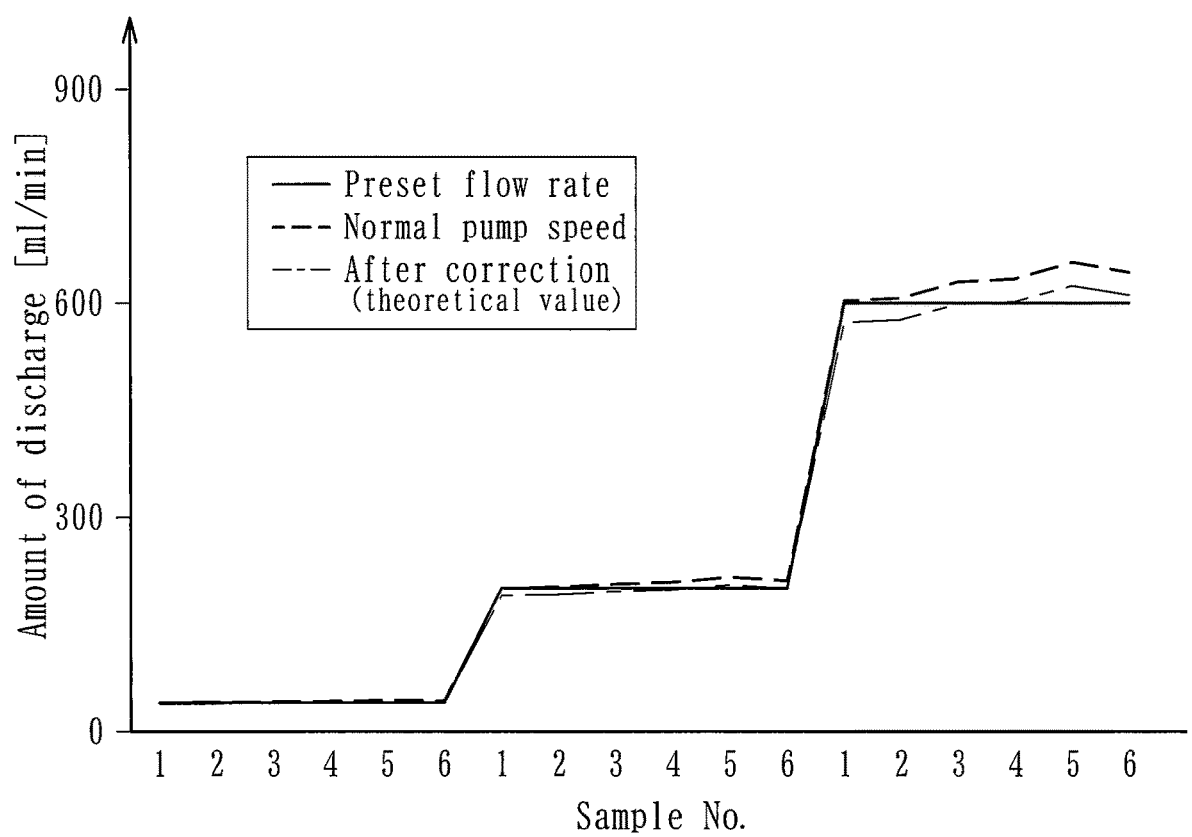

| Sample | Inside Diameter | Outside Diameter | Material | Small diameter (−150mmHg) | | | | | |
|---|---|---|---|---|---|---|---|---|---|
| | | | | suction pressure | Preset flow rate [ml/min] | Actual flow rate [ml/min] | Error [%] | Amount of discharge at 15%-increased speed (estimation) [ml/min] | Error [%] |
| 1 | 6.45 | 9.55 | ME6002 | −150 | 40 | 38 | −5.0 | 38.57 | −3.6 |
| 2 | 6.45 | 9.55 | T-H8D | −150 | 40 | 39.5 | −1.3 | 40.09 | 0.2 |
| 3 | 6.6 | 9.7 | ME6002 | −150 | 40 | 39 | −2.5 | 39.59 | −1.0 |
| 4 | 6.6 | 9.7 | T-H8D | −150 | 40 | 41.5 | 3.8 | 42.12 | 5.3 |
| 5 | 6.75 | 9.85 | ME6002 | −150 | 40 | 40 | 0.0 | 40.60 | 1.5 |
| 6 | 6.75 | 9.85 | T-H8D | −150 | 40 | 42 | 5.0 | 42.63 | 6.6 |
| 1 | 6.45 | 9.55 | ME6002 | −150 | 200 | 184 | −8.0 | 186.76 | −6.6 |
| 2 | 6.45 | 9.55 | T-H8D | −150 | 200 | 194.5 | −2.8 | 197.42 | −1.3 |
| 3 | 6.6 | 9.7 | ME6002 | −150 | 200 | 188.75 | −5.6 | 191.58 | −4.2 |
| 4 | 6.6 | 9.7 | T-H8D | −150 | 200 | 200.5 | 0.3 | 203.51 | 1.8 |
| 5 | 6.75 | 9.85 | ME6002 | −150 | 200 | 198 | −1.0 | 200.97 | 0.5 |
| 6 | 6.75 | 9.85 | T-H8D | −150 | 200 | 203.25 | 1.6 | 206.30 | 3.1 |
| 1 | 6.45 | 9.55 | ME6002 | −150 | 350 | 332 | −5.1 | 336.98 | −3.7 |
| 2 | 6.45 | 9.55 | T-H8D | −150 | 350 | 342.75 | −2.1 | 347.89 | −0.6 |
| 3 | 6.6 | 9.7 | ME6002 | −150 | 350 | 338.25 | −3.4 | 343.32 | −1.9 |
| 4 | 6.6 | 9.7 | T-H8D | −150 | 350 | 358.25 | 2.4 | 363.62 | 3.9 |
| 5 | 6.75 | 9.85 | ME6002 | −150 | 350 | 351 | 0.3 | 356.27 | 1.8 |
| 6 | 6.75 | 9.85 | T-H8D | −150 | 350 | 364.75 | 4.2 | 370.22 | 5.8 |

[ Fig. 12 ]

[ Fig. 13 ]
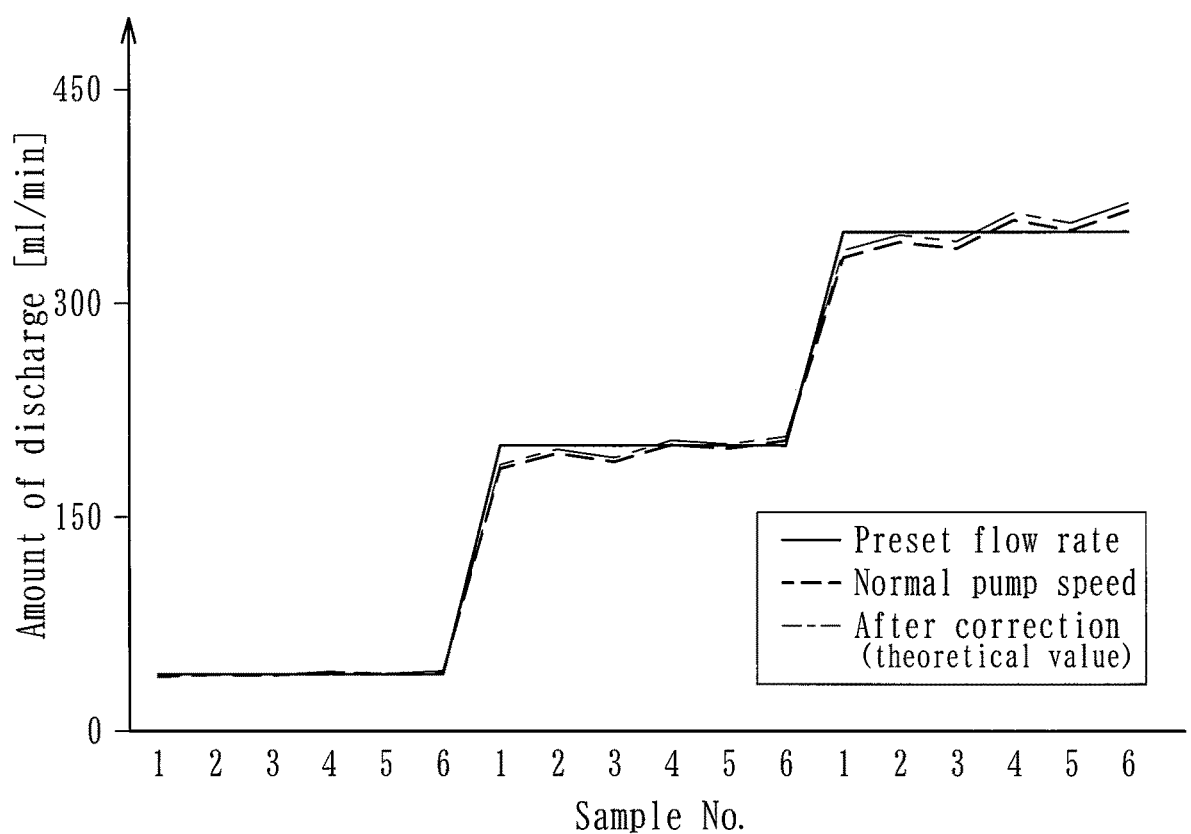

| Sample | Inside Diameter | Outside Diameter | Material | Large diameter (-150mmHg) | | | | Amount of discharge at 5%-increased speed (estimation) [ml/min] | Error [%] |
|---|---|---|---|---|---|---|---|---|---|
| | | | | suction pressure | Preset flow rate [ml/min] | Actual flow rate [ml/min] | Error [%] | | |
| 1 | 7.85 | 12.1 | ME6002 | -150 | 40 | 36.75 | -8.1 | 38.59 | -3.5 |
| 2 | 7.85 | 12.1 | T-H8D | -150 | 40 | 38.5 | -3.8 | 40.43 | 1.1 |
| 3 | 8 | 12.2 | ME6002 | -150 | 40 | 37 | -7.5 | 38.85 | -2.9 |
| 4 | 8 | 12.2 | T-H8D | -150 | 40 | 38.75 | -3.1 | 40.69 | 1.7 |
| 5 | 8.15 | 12.4 | ME6002 | -150 | 40 | 39 | -2.5 | 40.95 | 2.4 |
| 6 | 8.15 | 12.4 | T-H8D | -150 | 40 | 39 | -2.5 | 40.95 | 2.4 |
| 1 | 7.85 | 12.1 | ME6002 | -150 | 200 | 182 | -9.0 | 191.10 | -4.5 |
| 2 | 7.85 | 12.1 | T-H8D | -150 | 200 | 187.75 | -6.1 | 197.14 | -1.4 |
| 3 | 8 | 12.2 | ME6002 | -150 | 200 | 185 | -7.5 | 194.25 | -2.9 |
| 4 | 8 | 12.2 | T-H8D | -150 | 200 | 194 | -3.0 | 203.70 | 1.8 |
| 5 | 8.15 | 12.4 | ME6002 | -150 | 200 | 193.5 | -3.3 | 203.18 | 1.6 |
| 6 | 8.15 | 12.4 | T-H8D | -150 | 200 | 193.25 | -3.4 | 202.91 | 1.5 |
| 1 | 7.85 | 12.1 | ME6002 | -150 | 600 | 555 | -7.5 | 582.75 | -2.9 |
| 2 | 7.85 | 12.1 | T-H8D | -150 | 600 | 572 | -4.7 | 600.60 | 0.1 |
| 3 | 8 | 12.2 | ME6002 | -150 | 600 | 571.25 | -4.8 | 599.81 | 0.0 |
| 4 | 8 | 12.2 | T-H8D | -150 | 600 | 594 | -1.0 | 623.70 | 4.0 |
| 5 | 8.15 | 12.4 | ME6002 | -150 | 600 | 593.5 | -1.1 | 623.18 | 3.9 |
| 6 | 8.15 | 12.4 | T-H8D | -150 | 600 | 594.5 | -0.9 | 624.23 | 4.0 |

[ Fig. 14 ]

[ Fig. 15 ]
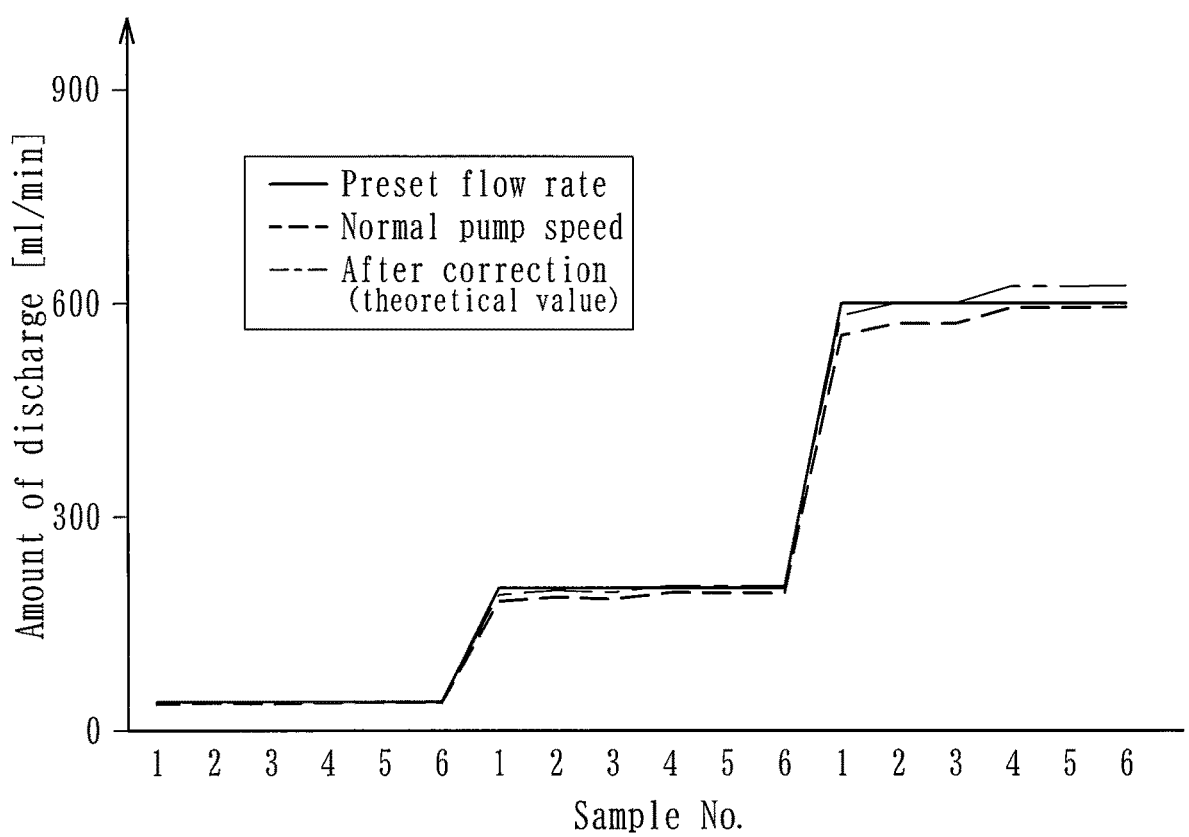

[ Fig. 16 ]

| | | | | Small diameter (+150mmHg) | | | | | |
|---|---|---|---|---|---|---|---|---|---|
| Sample | Inside Diameter | Outside Diameter | Material | suction pressure | Preset flow rate [ml/min] | Actual flow rate [ml/min] | Error [%] | Amount of discharge at 15%-reduced speed (estimation) [ml/min] | Error [%] |
| 1 | 6.45 | 9.55 | ME6002 | +150 | 40 | 42.25 | 13.1 | 38.46 | -3.8 |
| 2 | 6.45 | 9.55 | T-H8D | +150 | 40 | 44.5 | 11.3 | 37.83 | -5.4 |
| 3 | 6.6 | 9.7 | ME6002 | +150 | 40 | 46.75 | 16.9 | 39.74 | -0.7 |
| 4 | 6.6 | 9.7 | T-H8D | +150 | 40 | 46.75 | 16.9 | 39.74 | -0.7 |
| 5 | 6.75 | 9.85 | ME6002 | +150 | 40 | 48.75 | 21.9 | 41.44 | 3.6 |
| 6 | 6.75 | 9.85 | T-H8D | +150 | 40 | 47.25 | 18.1 | 40.16 | 0.4 |
| 1 | 6.45 | 9.55 | ME6002 | +150 | 200 | 224.5 | 12.3 | 190.83 | -4.6 |
| 2 | 6.45 | 9.55 | T-H8D | +150 | 200 | 223 | 11.5 | 189.55 | -5.2 |
| 3 | 6.6 | 9.7 | ME6002 | +150 | 200 | 233 | 16.5 | 198.05 | -1.0 |
| 4 | 6.6 | 9.7 | T-H8D | +150 | 200 | 234.75 | 17.4 | 199.54 | -0.2 |
| 5 | 6.75 | 9.85 | ME6002 | +150 | 200 | 241.75 | 20.9 | 205.49 | 2.7 |
| 6 | 6.75 | 9.85 | T-H8D | +150 | 200 | 239.25 | 19.6 | 203.36 | 1.7 |
| 1 | 6.45 | 9.55 | ME6002 | +150 | 350 | 394 | 12.6 | 334.90 | -4.3 |
| 2 | 6.45 | 9.55 | T-H8D | +150 | 350 | 390.75 | 11.6 | 332.14 | -5.1 |
| 3 | 6.6 | 9.7 | ME6002 | +150 | 350 | 408.75 | 16.8 | 347.44 | -0.7 |
| 4 | 6.6 | 9.7 | T-H8D | +150 | 350 | 409.75 | 17.1 | 348.29 | -0.5 |
| 5 | 6.75 | 9.85 | ME6002 | +150 | 350 | 421.25 | 20.4 | 358.06 | 2.3 |
| 6 | 6.75 | 9.85 | T-H8D | +150 | 350 | 417 | 19.1 | 354.45 | 1.3 |

[ Fig. 17 ]
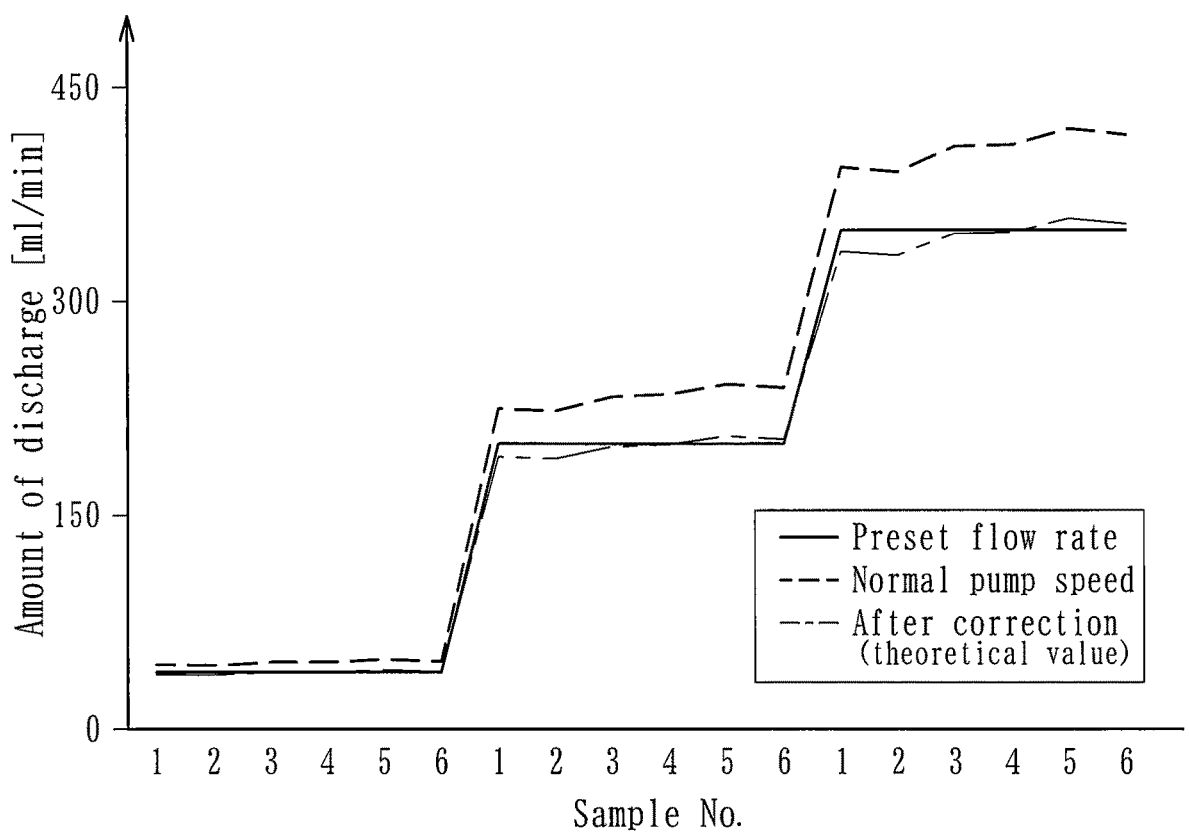

| Sample | Large diameter (+150mmHg) | | | | | | | |
|---|---|---|---|---|---|---|---|---|
| | Inside Diameter | Outside Diameter | Material | suction pressure | Preset flow rate [ml/min] | Actual flow rate [ml/min] | Error [%] | Amount of discharge at 10%-reduced speed (estimation) [ml/min] | Error [%] |
| 1 | 7.85 | 12.1 | ME6002 | +150 | 40 | 42.5 | 6.3 | 38.25 | -4.4 |
| 2 | 7.85 | 12.1 | T-H8D | +150 | 40 | 42.5 | 6.3 | 38.25 | -4.4 |
| 3 | 8 | 12.2 | ME6002 | +150 | 40 | 44.75 | 11.9 | 40.28 | 0.7 |
| 4 | 8 | 12.2 | T-H8D | +150 | 40 | 43.75 | 9.4 | 39.38 | -1.6 |
| 5 | 8.15 | 12.4 | ME6002 | +150 | 40 | 46.75 | 16.9 | 42.08 | 5.2 |
| 6 | 8.15 | 12.4 | T-H8D | +150 | 40 | 45 | 12.5 | 40.50 | 1.3 |
| 1 | 7.85 | 12.1 | ME6002 | +150 | 200 | 209.5 | 4.8 | 188.55 | -5.7 |
| 2 | 7.85 | 12.1 | T-H8D | +150 | 200 | 213.5 | 6.8 | 192.15 | -3.9 |
| 3 | 8 | 12.2 | ME6002 | +150 | 200 | 221.5 | 10.8 | 199.35 | -0.3 |
| 4 | 8 | 12.2 | T-H8D | +150 | 200 | 220.75 | 10.4 | 198.68 | -0.7 |
| 5 | 8.15 | 12.4 | ME6002 | +150 | 200 | 230.5 | 15.3 | 207.45 | 3.7 |
| 6 | 8.15 | 12.4 | T-H8D | +150 | 200 | 225.5 | 12.8 | 202.95 | 1.5 |
| 1 | 7.85 | 12.1 | ME6002 | +150 | 600 | 643 | 7.2 | 578.70 | -3.5 |
| 2 | 7.85 | 12.1 | T-H8D | +150 | 600 | 640 | 6.7 | 576.00 | -4.0 |
| 3 | 8 | 12.2 | ME6002 | +150 | 600 | 662.25 | 10.4 | 596.03 | -0.7 |
| 4 | 8 | 12.2 | T-H8D | +150 | 600 | 664.5 | 10.8 | 598.05 | -0.3 |
| 5 | 8.15 | 12.4 | ME6002 | +150 | 600 | 694.75 | 15.8 | 625.28 | 4.2 |
| 6 | 8.15 | 12.4 | T-H8D | +150 | 600 | 671.75 | 12.0 | 604.58 | 0.8 |

[ Fig. 18 ]

[ Fig. 19 ]
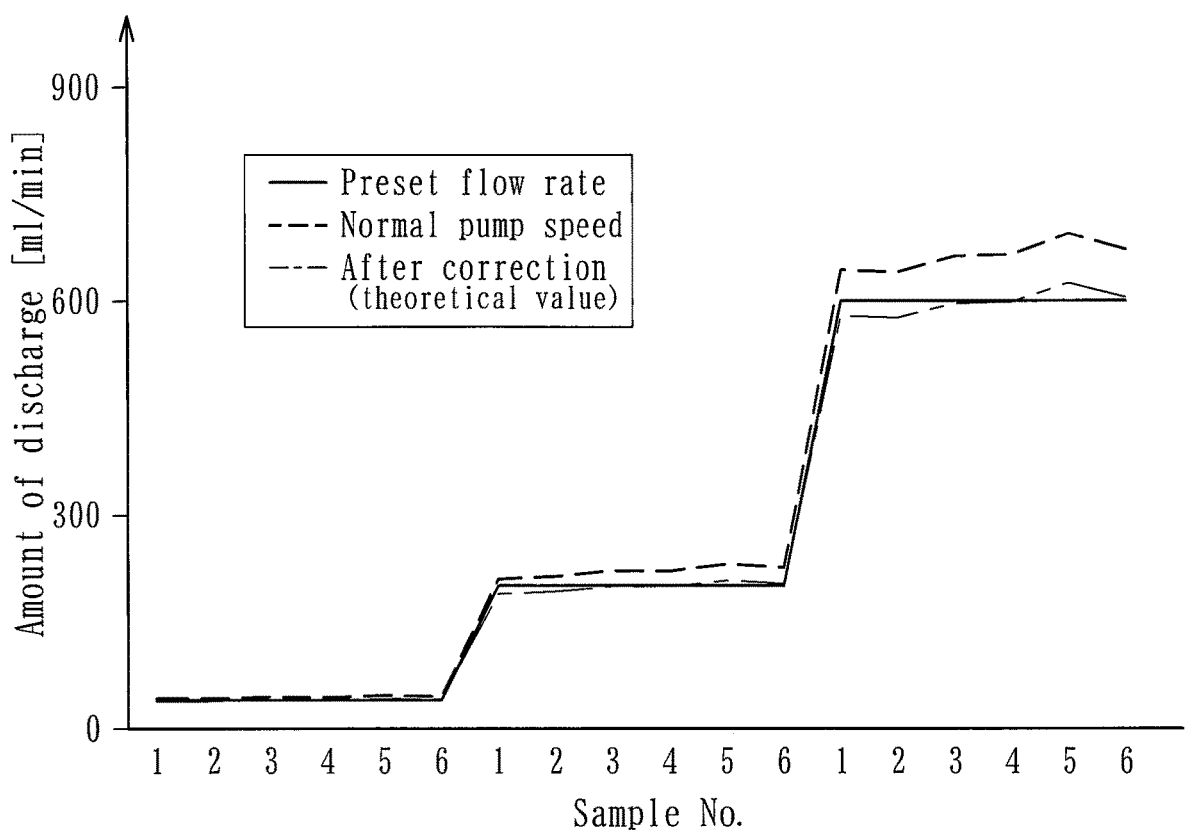

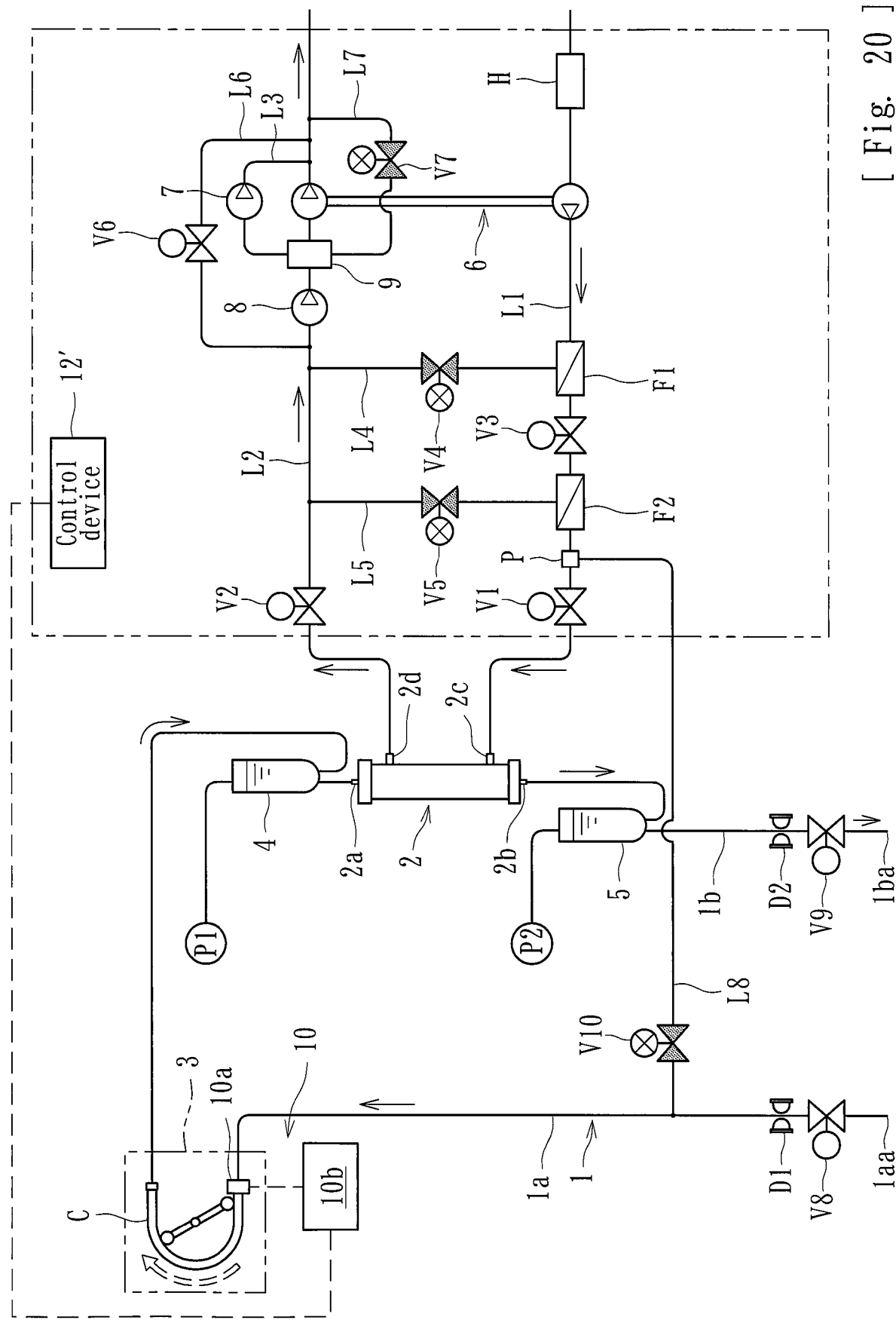
[Fig. 20]

[ Fig. 21 ]
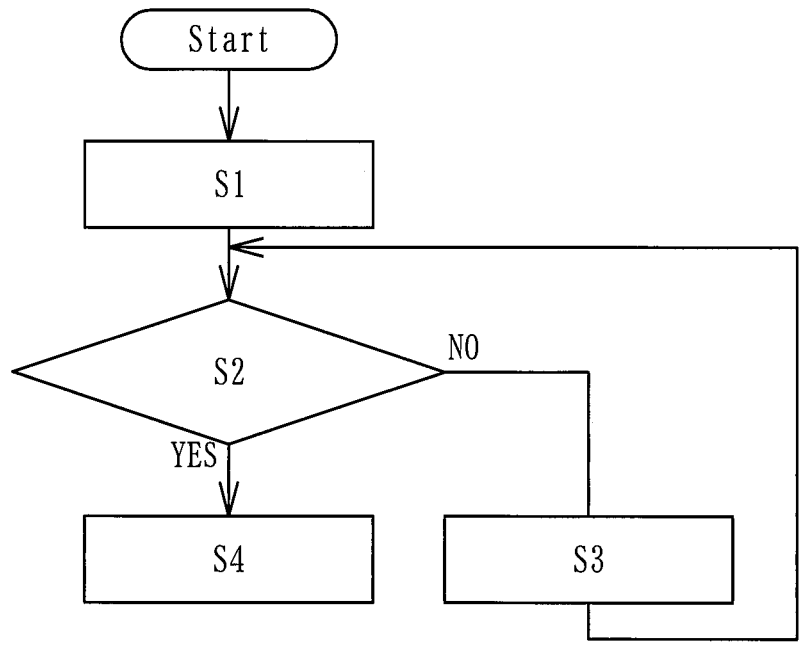
S1: Activate blood pump
S2: Is suction pressure predetermined value?
S3: Correct driving speed
S4: Maintain driving speed

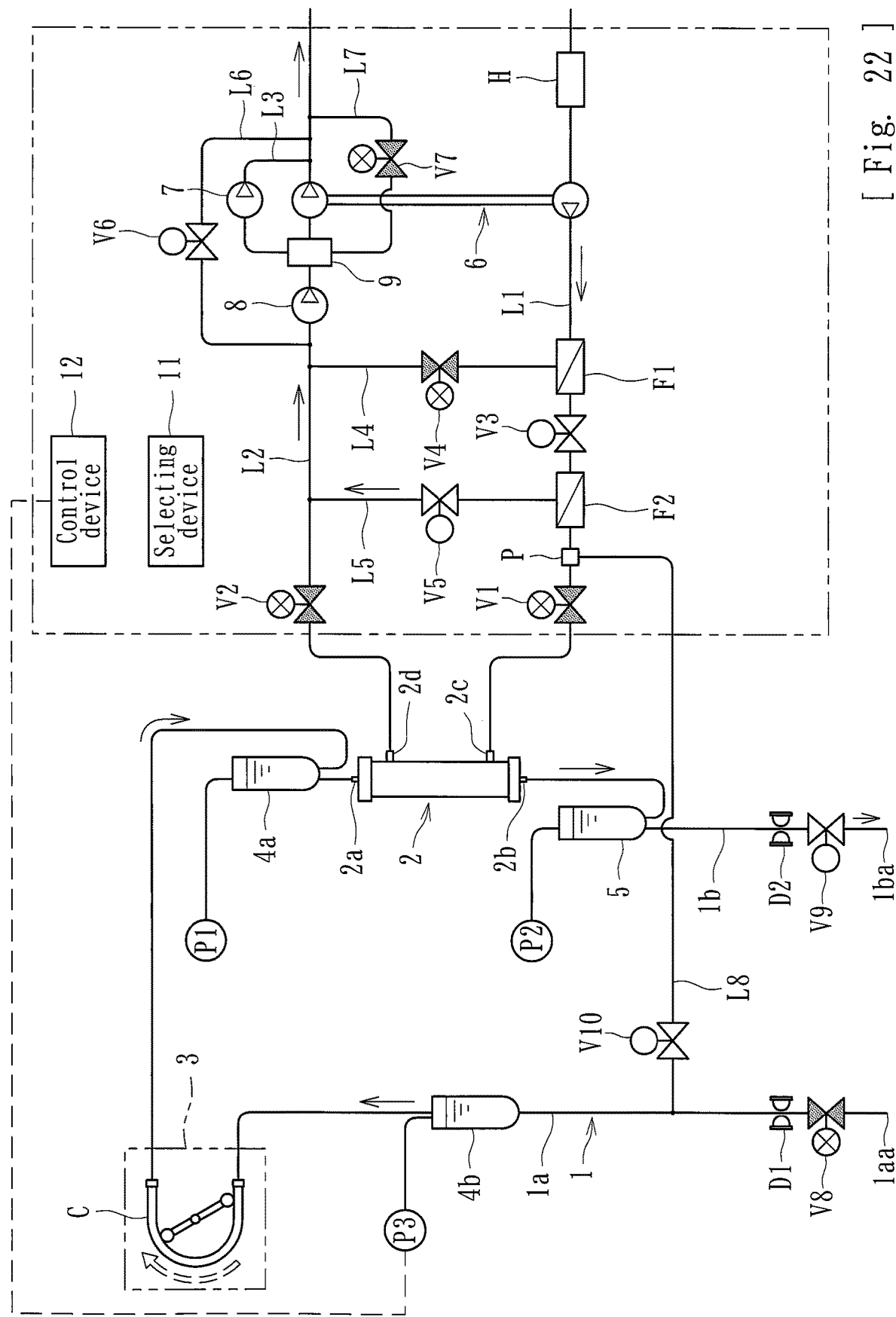
[ Fig. 22 ]

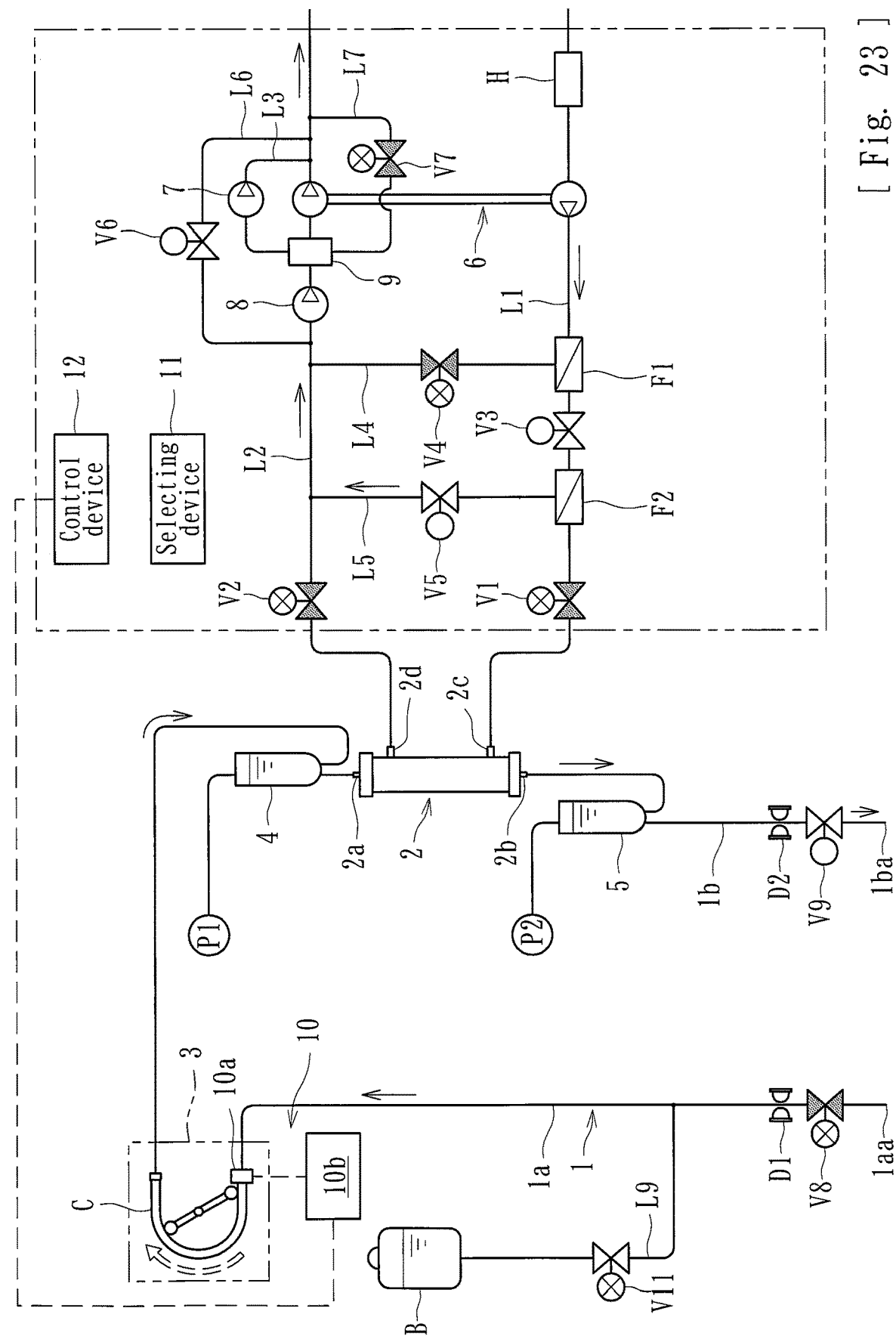
[Fig. 23]

[Fig. 24]
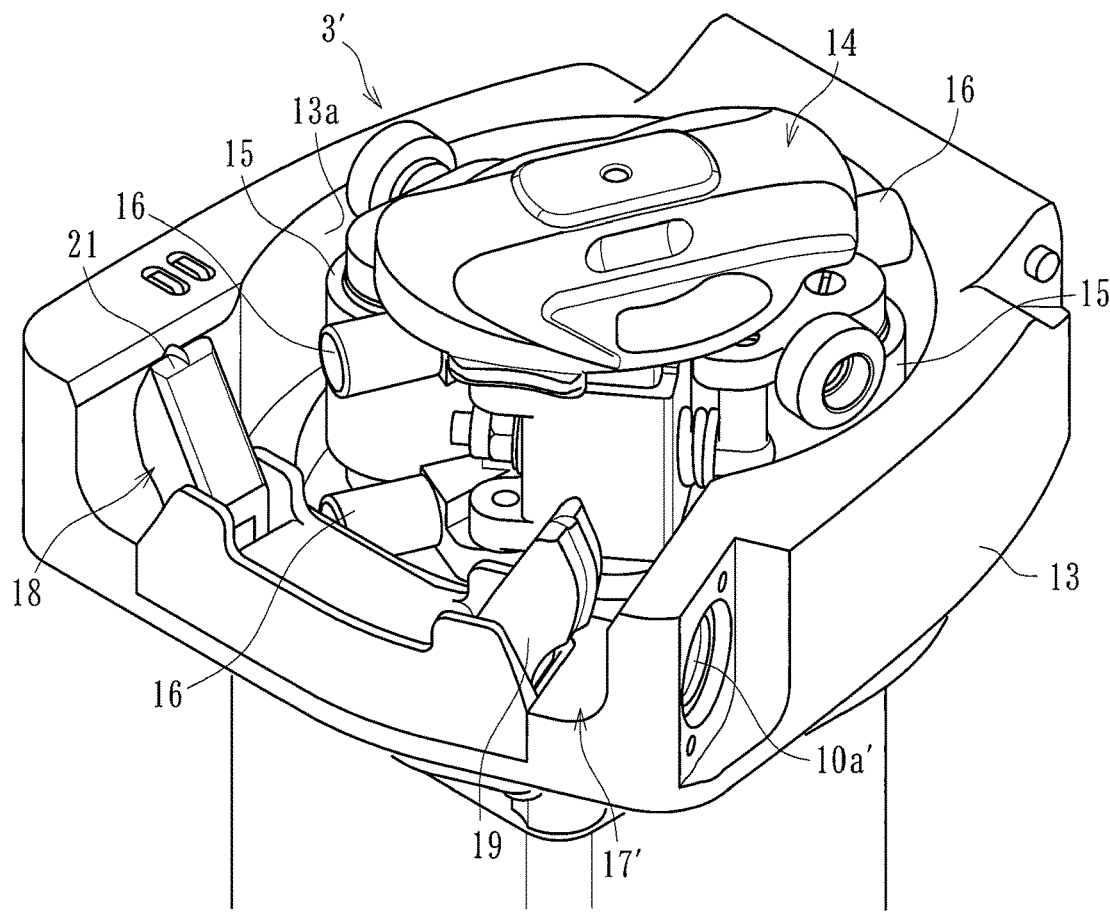
[Fig. 25]
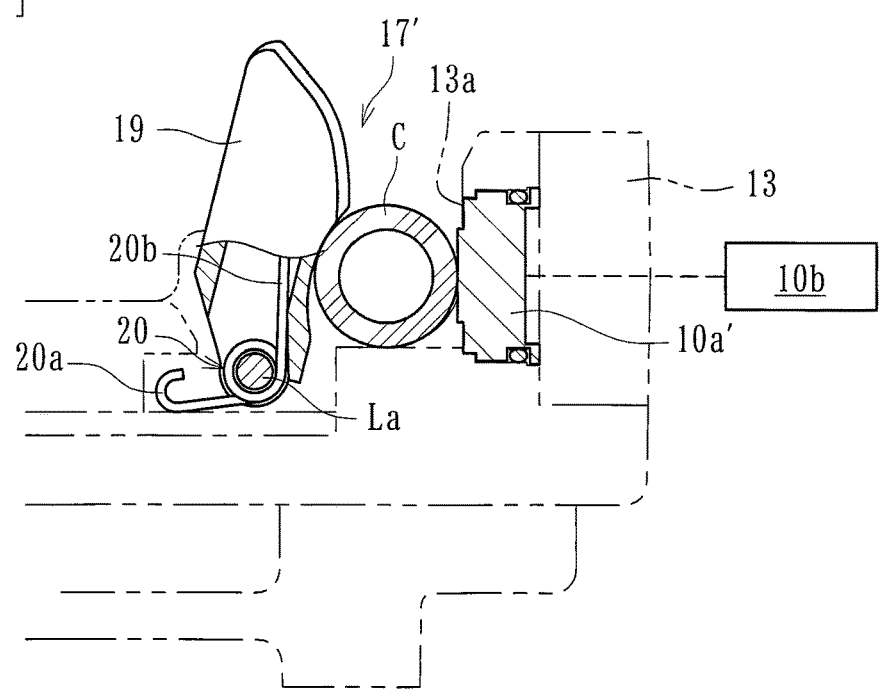

BLOOD PURIFICATION APPARATUS

FIELD

The present teachings relate to a blood purification apparatus that includes a blood circuit including an arterial blood circuit and a venous blood circuit to distal ends of which puncture needles are connectable, respectively, and through which the blood of a patient is extracorporeally circulated; a blood purification device connected to proximal ends of the arterial blood circuit and the venous blood circuit and that purifies the blood extracorporeally circulating through the blood circuit; a blood pump allowing liquid in a squeezable tube connected to the arterial blood circuit to flow by squeezing the squeezable tube in the lengthwise direction while compressing the squeezable tube in the radial direction; and a pressure-detecting device attached to a predetermined position of the arterial blood circuit that is on the distal side with respect to the position where the blood pump is provided, the pressure-detecting device being capable of detecting the suction pressure of the blood pump.

BACKGROUND

A typical blood circuit intended for hemodialysis treatment basically includes an arterial blood circuit to the distal end of which an arterial puncture needle is attached, and a venous blood circuit to the distal end of which a venous puncture needle is attached. A blood purifier such as a dialyzer is connectable to the proximal end of the arterial blood circuit and to the proximal end of the venous blood circuit. The arterial blood circuit is provided with a blood pump. When the blood pump is activated with both the arterial puncture needle and the venous puncture needle being stuck in a patient, blood is collected through the arterial puncture needle. The collected blood is caused to flow through the arterial blood circuit and is introduced into the dialyzer. Then, the blood purified by the dialyzer is caused to flow through the venous blood circuit and is returned into the body of the patient through the venous puncture needle. Thus, dialysis treatment is performed.

In general, the blood pump is a peristaltic pump including a roller that is capable of causing liquid flowing in a squeezable tube connected to the arterial blood circuit to flow by squeezing the squeezable tube in the lengthwise direction while closing the flow route by compressing the squeezable tube in the radial direction. In such a blood pump, the amount of blood to be extracorporeally circulated is determined in accordance with the amount of discharge per revolution of the roller and the number of revolutions of the roller per hour. Therefore, to perform the blood purification treatment efficiently and in a good manner, the amount of discharge from the blood pump needs to be kept constant.

Accordingly, for example, a jig for adjusting the size of a gap between the roller and a stator is used in the known art, so that the size of the gap is adjusted as predetermined (as set for the squeezable tube to be attached). Therefore, when the squeezable tube is attached to the stator, the flow route is assuredly closed by the roller (that is, the flow route is assuredly closed by being compressed by the roller). Thus, the amount of discharge from the blood pump can be kept constant, and the blood purification treatment can be performed efficiently and in a good manner. Such a technique has not been disclosed by any publicly known teaching, and there is no information on patent literature to be cited.

SUMMARY

In the above known blood purification apparatus, the size of the gap provided in the blood pump may be adjusted accurately. However, if, for example, a substitution line that allows a predetermined substitution fluid to be supplied is provided at a position of the arterial blood circuit that is on the distal side with respect to a position where the blood pump is provided, a problem arises in that the suction pressure of the blood pump changes with the flow rate, the liquid pressure, or the like of the substitution fluid that is fed into the substitution line, and the amount of discharge consequently has an error. Such a problem occurs not only in the blood purification apparatus including the substitution line but also in blood purification apparatuses of various types in which the suction pressure of the blood pump changes.

The present teachings have been conceived in view of the above circumstances and provides a blood purification apparatus in which the error in the amount of discharge from a blood pump that is caused by the change in the suction pressure of the blood pump is reduced.

According to the teaching herein, there is provided a blood purification apparatus that includes a blood circuit including an arterial blood circuit and a venous blood circuit to distal ends of which puncture needles are connectable, respectively, and through which blood of a patient is extracorporeally circulated; a blood purification device connected to proximal ends of the arterial blood circuit and the venous blood circuit and that purifies the blood extracorporeally circulating through the blood circuit; a squeezable tube connected to the arterial blood circuit; a blood pump allowing liquid in the squeezable tube to flow by squeezing the squeezable tube in a lengthwise direction while compressing the squeezable tube in a radial direction; and a pressure-detecting device attached to a predetermined position of the arterial blood circuit that is on a distal side with respect to a position where the blood pump is provided, the pressure-detecting device being capable of detecting a suction pressure of the blood pump. Furthermore, the blood purification apparatus includes a control device capable of controlling a driving speed of the blood pump in accordance with the suction pressure of the blood pump that is detected by the pressure-detecting device.

According to the teachings herein, the blood purification apparatus taught herein further includes a substitution line connected to a position of the arterial blood circuit that is on the distal side with respect to the position where the blood pump is provided, the substitution line allowing a predetermined substitution fluid to be supplied to the arterial blood circuit. The control device is capable of controlling a flow rate of the substitution fluid supplied from the substitution line such that the suction pressure of the blood pump becomes a predetermined value.

According to the teachings herein, in the blood purification apparatus taught herein, the control device is capable of controlling the driving speed of the blood pump in accordance with a characteristic regarding an amount of discharge from the squeezable tube.

According to the teachings herein. In the blood purification apparatus taught herein, the control device controls the driving speed of the blood pump by feeding back the suction pressure of the blood pump that is detected by the pressure-detecting device.

According to the teachings herein, in the blood purification apparatus taught herein, the pressure-detecting device is attached to the blood pump and includes a displacement-detecting device that detects a radial displacement of the squeezable tube; and a pressure-calculating device that is capable of calculating a pressure in a liquid flow route in accordance with the radial displacement of the squeezable tube that is detected by the displacement-detecting device.

According to the teachings herein, the blood purification apparatus includes the control device capable of controlling the driving speed of the blood pump in accordance with the suction pressure of the blood pump that is detected by the pressure-detecting device. Therefore, the error in the amount of discharge that is caused by the change in the suction pressure of the blood pump can be reduced.

According to the teachings herein, the blood purification apparatus further includes the substitution line connected to the position of the arterial blood circuit that is on the distal side with respect to the position where the blood pump is provided, the substitution line allowing the predetermined substitution fluid to be supplied to the arterial blood circuit. Furthermore, the control device is capable of controlling the flow rate of the substitution fluid supplied from the substitution line such that the suction pressure of the blood pump becomes the predetermined value. Therefore, the error in the amount of discharge that is caused by the change in the suction pressure of the blood pump can be reduced quicker and more smoothly.

According to the teachings herein, the control device is capable of controlling the driving speed of the blood pump in accordance with the characteristic regarding the amount of discharge from the squeezable tube. Therefore, the error in the amount of discharge that is caused by the change n the suction pressure of the blood pump can be reduced more easily and more smoothly. In addition, the driving speed of the blood pump can be set with consideration for the diameter of the squeezable tube.

According to the teachings herein, the control device controls the driving speed of the blood pump by feeding back the suction pressure of the blood pump that is detected by the pressure-detecting device. Therefore, the error in the amount of discharge that is caused by the change in the suction pressure of the blood pump can be reduced more accurately.

According to the teachings herein, the pressure-detecting device is attached to the blood pump and includes the displacement-detecting device that detects the radial displacement of the squeezable tube, and the pressure-calculating device that is capable of calculating the pressure in the liquid flow route in accordance with the radial displacement of the squeezable tube that s detected by the displacement-detecting device. Therefore, no additional pressure-detecting device needs to be provided to an element other than the blood pump, providing ease of handling.

BRIEF DESCRIPTION OF THE DRAWINGS

FIG. 1 is a schematic diagram of a blood purification apparatus according to a first embodiment of the present teaching.

FIG. 2 is a perspective view of a blood pump applied to the blood purification apparatus.

FIG. 3 is a plan view of the blood pump.

FIG. 4 is a schematic sectional view of a pressure-detecting device provided to the blood pump.

FIG. 5 is a schematic diagram of the blood purification apparatus in which the blood pump is in normal operation.

FIG. 6 is a schematic diagram of the blood purification apparatus in which the blood pump is in correcting operation (substituting operation).

FIG. 7 is a flow chart of a control process performed in the blood purification apparatus.

FIG. 8 is a table summarizing results of an experiment (an experiment conducted with samples having small diameters and at a suction pressure of 0 mmHg) for demonstrating technical advantages of the blood purification apparatus.

FIG. 9 is a graph based on the table illustrated in FIG. 8.

FIG. 10 is a table summarizing results of another experiment (an experiment conducted with samples having large diameters and at a suction pressure of 0 mmHg) for demonstrating technical advantages of the blood purification apparatus.

FIG. 11 is a graph based on the table illustrated in FIG. 10.

FIG. 12 is a table summarizing results of yet another experiment (an experiment conducted with samples having small diameters and at a suction pressure of −150 mmHg) for demonstrating technical advantages of the blood purification apparatus.

FIG. 13 is a graph based on the table illustrated in FIG. 12.

FIG. 14 is a table summarizing results of yet another experiment (an experiment conducted with samples having large diameters and at a suction pressure of −150 mmHg) for demonstrating technical advantages of the blood purification apparatus.

FIG. 15 is a graph based on the table illustrated in FIG. 14.

FIG. 16 is a table summarizing results of yet another experiment (an experiment conducted with samples having small diameters and at a suction pressure of +150 mmHg) for demonstrating technical advantages of the blood purification apparatus.

FIG. 17 is a graph based on the table illustrated in FIG. 16.

FIG. 18 is a table summarizing results of yet another experiment (an experiment conducted with samples having large diameters and at a suction pressure of +150 mmHg) for demonstrating technical advantages of the blood purification apparatus.

FIG. 19 is a graph based on the table illustrated in FIG. 18.

FIG. 20 is a schematic diagram of a blood purification apparatus according to a second embodiment of the present teaching.

FIG. 21 is a flow chart of a control process performed in the blood purification apparatus.

FIG. 22 is a schematic diagram of a blood purification apparatus according to another embodiment of the present teaching.

FIG. 23 is a schematic diagram of a blood purification apparatus according to yet another embodiment of the present teaching.

FIG. 24 is a perspective view of a blood pump according to yet another embodiment.

FIG. 25 is a schematic sectional view of a pressure-detecting device provided to the blood pump.

DETAILED DESCRIPTION

Embodiments of the present teaching will now be described specifically with reference to the drawings.

A blood purification apparatus according to a first embodiment is intended for giving blood purification treatment (such as hemodialysis treatment) by extracorporeally circulating the blood of a patient and includes, as illustrated in FIG. 1, a blood circuit 1 including an arterial blood circuit 1a to a distal end 1aa of which an arterial puncture needle (not illustrated) is connectable and a venous blood circuit 1b to a distal end 1*ba* of which a venous puncture needle (not illustrated) is connectable, the blood circuit 1 allowing the blood of the patient to extracorporeally circulate therethrough; a dialyzer 2 (a blood purification device) connected to a proximal end of the arterial blood circuit 1*a* and to a proximal end of the venous blood circuit 1*b* and that purifies the blood flowing in the blood circuit 1; a blood pump 3 provided to the arterial blood circuit 1*a*; an arterial air-trap chamber 4 provided to the arterial blood circuit 1*a*; a venous air-trap chamber 5 provided to the venous blood circuit 1*b*; a dialysate introduction line L1 through which dialysate is introduced into the dialyzer 2; a dialysate drain line L2 through which drain liquid is discharged from the dialyzer 2; a substitution line L8; a selecting device 11; and a control device 12.

The arterial blood circuit 1*a* is provided with a connector (not illustrated) at the distal end 1*aa* thereof, and the arterial puncture needle is connectable to the distal end 1*aa* with the connector interposed therebetween. The blood pump 3, which is of a peristaltic type, and the arterial air-trap chamber 4 are provided at respective halfway positions of the arterial blood circuit 1*a*. The arterial blood circuit 1*a* and the venous blood circuit 1*b* are provided at distal portions thereof with respective clamping devices (such as electromagnetic valves V8 and V9) that are capable of closing respective flow routes. The venous blood circuit 1*b* is provided with a connector (not illustrated) at the distal end 1*ba* thereof, and the venous puncture needle is connectable to the distal end 1*ba* with the connector interposed therebetween. The venous air-trap chamber 5 is provided at a halfway position of the venous blood circuit 1*b*.

The arterial air-trap chamber 4 and the venous air-trap chamber 5 are provided with respective pressure sensors (P1 and P2) that are each capable of detecting the pressure in an upper part (an air layer) of a corresponding one of the chambers. The pressure sensor P1 provided to the arterial air-trap chamber 4 is capable of detecting the pressure (liquid pressure) at that position of the arterial blood circuit 1*a*. The pressure sensor P2 provided to the venous air-trap chamber 5 is capable of detecting the pressure (liquid pressure) at that position of the venous blood circuit 1*b*.

When the blood pump 3 is activated (to undergo normal rotation) in a state where the arterial puncture needle connected to the distal end 1*aa* of the arterial blood circuit 1*a* and the venous puncture needle connected to the distal end 1*ba* of the venous blood circuit 1*b* are stuck in the patient, the blood of the patient flows through the arterial blood circuit 1*a* while undergoing bubble removal (while bubbles contained therein are removed) in the arterial air-trap chamber 4 and reaches the dialyzer 2, where the blood is purified. Then, the blood undergoes bubble removal (bubbles contained therein are removed) in the venous air-trap chamber 5, flows through the venous blood circuit 1*b*, and returns into the body of the patient. Thus, the blood of the patient can be purified by the dialyzer 2 while being extracorporeally circulated through the blood circuit 1 from the distal end 1*aa* of the arterial blood circuit 1*a* to the distal end 1*ba* of the venous blood circuit 1*b*.

The arterial blood circuit 1*a* is provided with a squeezable tube C at a halfway position thereof. The squeezable tube C is attachable to the blood pump 3. While the squeezable tube C is compressed in the radial direction by rollers 15 (squeezing units) included in the blood pump 3 (a peristaltic pump), to be described below, such that the flow route provided therein is closed, the squeezable tube C is squeezed in the lengthwise direction, whereby liquid in the squeezable tube C is caused to flow in the direction of rotation of a rotor 14.

The squeezable tube C is a flexible tube that is softer and has a larger diameter than other flexible tubes forming the arterial blood circuit 1*a*.

The dialyzer 2 has, in a housing thereof, a blood inlet 2*a* (a blood introduction port), a blood outlet 2*b* (a blood delivery port), a dialysate inlet 2*c* (an inlet of the dialysate flow route, or a dialysate introduction port), and a dialysate outlet 2*d* (an outlet of the dialysate flow route, or a dialysate delivery port). The arterial blood circuit 1*a* is connected to the blood inlet 2*a*. The venous blood circuit 1*b* is connected to the blood outlet 2*b*. The dialysate inlet 2*c* and the dialysate outlet 2*d* are connected to the dialysate introduction line L1 and the dialysate drain line L2, respectively.

The dialyzer 2 houses a plurality of hollow fiber membranes (not illustrated), and such hollow fibers serve as blood purification membranes for purifying the blood. The blood purification membranes in the dialyzer 2 define blood flow routes (each extending between the blood inlet 2*a* and the blood outlet 2*b*) in which the blood of the patient flows and dialysate flow routes (each extending between the dialysate inlet 2*c* and the dialysate outlet 2*d*) in which the dialysate flows. Typically, the blood flows on the inside of each of the hollow fibers, and the dialysate flows on the outside of the hollow fibers. The hollow fiber membranes serving as the blood purification membranes each have a number of very small holes (pores) extending therethrough from the outer peripheral surface to the inner peripheral surface. Hence, impurities and the like contained in the blood are allowed to penetrate through the membranes into the dialysate.

The arterial blood circuit 1*a* and the venous blood circuit 1*b* according to the first embodiment are further provided at the distal portions thereof with respective bubble-detecting devices (D1 and D2) capable of detecting gas (bubbles) contained in the blood flowing in the arterial blood circuit 1*a* and the venous blood circuit 1*b* during the blood purification treatment. The bubble-detecting devices (D1 and D2) are each provided in a predetermined unit together with, for example, a blood-checking device, which is not illustrated, and the clamping device (V8 or V9).

The bubble-detecting devices (D1 and D2) are each a sensor capable of detecting bubbles (air) flowing in the flexible tube that forms the arterial blood circuit 1*a* or the venous blood circuit 1*b*. The bubble-detecting devices (D1 and D2) each include, for example, an ultrasonic vibration element formed of a piezoelectric element, and an ultrasonic receiving element formed of a piezoelectric element. The bubble-detecting devices (D1 and D2) are each capable of emitting ultrasonic waves from the ultrasonic vibration element toward the flexible tube forming the arterial blood circuit 1*a* or the venous blood circuit 1*b* and is also capable of receiving the thus generated vibration by the ultrasonic receiving element.

The ultrasonic receiving element is configured such that the voltage changes with the vibration received. The ultrasonic receiving element is capable of detecting the flow of bubbles by the fact that the detected voltage has exceeded a predetermined threshold. Specifically, the ultrasonic attenuation factor of bubbles is higher than those of blood and substitution solutions. Hence, the ultrasonic waves transmitted through the liquid are detected. Then, if the detected voltage has exceeded the predetermined threshold, it is regarded that the flow of bubbles (gas) has been detected.

The dialysate introduction line L1 and the dialysate drain line L2 are provided with a duplex pump 6 that delivers a dialysate prepared to have a predetermined concentration to the dialyzer 2 and discharges waste products and the like (drain liquid) together with the dialysate from the dialyzer 2. Specifically, the duplex pump 6 is provided over the dialysate introduction line L1 and the dialysate drain line L2. When the duplex pump 6 is activated, the dialysate can be introduced into the dialyzer 2 through the dialysate introduction line L1, and the drain liquid can be discharged from the dialyzer 2 through the dialysate drain line L2.

The dialysate introduction line L1 is provided with electromagnetic valves V1 and V3 and filtration filters F1 and F2. The dialysate to be introduced into the dialyzer 2 can be filtered by the filtration filters F1 and F2, and the flow route of the dialysate is closable or openable at an arbitrary timing by the electromagnetic valves V1 and V3. The dialysate introduction line L1 is connected to the dialysate drain line L2 with bypass lines L4 and L5. The bypass lines L4 and L5 are provided with electromagnetic valves V4 and V5, respectively. Reference character H given in FIG. 1 denotes a heating device (a heater) for heating the dialysate to be supplied to the dialyzer 2 or to the blood circuit 1.

Furthermore, detour lines L3 and L6 for detouring the duplex pump 6 are connected to the dialysate drain line L2. The detour line L6 is provided with an electromagnetic valve V6. The detour line L3 is provided with an ultrafiltration pump 7. Hence, when the ultrafiltration pump 7 is activated in the process of extracorporeally circulating the blood of the patient through the blood circuit 1, ultrafiltration in which water is removed from the blood flowing through the dialyzer 2 can be performed.

Furthermore, the dialysate drain line L2 is provided with a pressurizing pump 8 at a position thereof on the upstream side (the left side in FIG. 1) with respect to the duplex pump 6. The pressurizing pump 8 adjusts the liquid pressure in the dialysate drain line L2 at the duplex pump 6. A release lie L7 extends from a position of the dialysate drain line L2 between the pressurizing pump 8 and the duplex pump 6, with a degassing chamber 9 interposed therebetween. The dialysate drain line 12 and the release line L7 branching off therefrom are provided with electromagnetic valves V2 and V7, respectively. Hence, the flow route of the dialysate is closable or openable at an arbitrary timing.

The substitution line L8 has one end thereof connected to a collecting port P (a sampling port) provided at a predetermined position of the dialysate introduction line L1 (in the first embodiment, between the electromagnetic valve V1 and the filtration filter F2) and the other end thereof connected to the arterial blood circuit 1a (to a position nearer to the distal end 1aa than the position where a pressure-detecting device 10 is provided). The substitution line L8 provides a flow route that allows the dialysate in the dialysate introduction line L1 to be supplied to the arterial blood circuit 1a. The substitution line L8 is provided with a clamping device V10. When the clamping device V10 is opened, the dialysate in the dialysate introduction line L1 can be supplied to the blood circuit 1 (the arterial blood circuit 1a). When the clamping device V10 is closed, the flow route can be closed.

As illustrated in FIGS. 2 to 4, the blood pump 3 according to the first embodiment basically includes a stator 13, the rotor 14 rotatable on the inner side of the stator 13, the rollers 15 (squeezing units) provided to the rotor 14, a pair of upper and lower guide pins 16, an upstream-side holding device 17, a downstream-side holding device 18, and a load sensor 10a (a displacement-detecting device) and a calculating device 10b (see FIG. 4) included in the pressure-detecting device. In the drawings, a cover provided over the stator 13 of the blood pump 3 is not illustrated.

The stator 13 has a fitting recess 13a into which the squeezable tube C is fitted. Therefore, the squeezable tube C can be fitted along the inner peripheral wall of the fitting recess 13a. The rotor 14, which is rotatably driven by a motor, is provided substantially at the center of the fitting recess 13a. The pair of rollers 15 and the guide pins 16 are provided on the side face (a surface facing the inner peripheral wall of the fitting recess 13a) of the rotor 14.

The rollers 15 are rotatable about respective rotating shafts M provided on the outer peripheral edge of the rotor 14. The rollers 15 compress the squeezable tube C fitted in the fitting recess 13a in the radial direction such that the flow route provided therein is closed, and also squeezes the squeezable tube C in the lengthwise direction (the direction in which the blood flows) with the rotation of the rotor 14, whereby the liquid such as blood is caused to flow in the arterial blood circuit 1a. Specifically, when the rotor 14 is rotated with the squeezable tube C fitted in the fitting recess 13a, the squeezable tube C is compressed between the rollers 15 and the inner peripheral wall of the fitting recess 13a, whereby the flow route therein is closed (stopped). Furthermore, with the rotation of the rotor 14, the squeezable tube C can be squeezed in the direction of rotation of the rotor 14 (in the lengthwise direction). With such a squeezing motion, the blood in the arterial blood circuit 1a is discharged in the direction of rotation of the rotor 14. Hence, the blood can be extracorporeally circulated through the blood circuit 1.

As illustrated in FIG. 2, the guide pins 16 are a pair of upper and lower pin-like members projecting from the upper end and the lower end, respectively, of the rotor 14 toward the inner peripheral wall of the fitting recess 13a. The squeezable tube C is held between the pair of upper and lower guide pins 16. Specifically, while the rotor 14 is rotated, the pair of upper and lower guide pins 16 retain the squeezable tube C at a proper position and prevent the squeezable tube C from being pushed upward from the fitting recess 13a.

The upstream-side holding device 17 is provided for holding the upstream side (a pert where the arterial blood circuit 1a of the distal end 1aa side is connected) of the squeezable tube C fitted in the fitting recess 13a of the stator 13 of the blood pump 3. As illustrated in FIGS. 2 to 4, the upstream-side holding device 17 includes a holding member 19 capable of holding the squeezable tube C while pressing the squeezable tube C in the radial direction, and a torsion spring 20 (an urging member) urging the holding member 19 toward the squeezable tube C.

As illustrated in FIG. 4, the holding member 19 is a component that is swingable about a swing shaft La. The holding member 19 is urged with a relatively large force in a holding direction by the torsion spring 20 and is capable of securing the squeezable tube C by firmly pinching the squeezable tube C while pressing the upstream part of the squeezable tube C. As illustrated in FIG. 4, the torsion spring 20 is attached to the swing shaft La and urges the holding member 19. The torsion spring 20 includes a fixed end 20a positioned on a fixed portion of the stator 13 (in the first embodiment, on the load sensor 10a attached to the stator 13), and a pressing end 20b pressing the holding member 19. Note that the torsion spring 20 may be replaced with any other urging member that urges the holding member 19.

The downstream-side holding device 18 is provided for holding the downstream side (a part where the arterial blood circuit 1a of the proximal end side (the dialyzer 2 side) is connected) of the squeezable tube C fitted in the fitting recess 13a of the stator 13 of the blood pump 3. The downstream-side holding device 18 includes a holding member 21 capable of holding the squeezable tube C while pressing the squeezable tube C in the radial direction, and a torsion spring 22 urging the holding member 21 toward the squeezable tube C.

As with the holding member 19 of the upstream-side holding device 17, the holding member 21 is a component that is swingable about a swing shaft Lb. The holding member 21 is urged with a relatively large force in a holding direction by the torsion spring 22 and is capable of securing the squeezable tube C by firmly pinching the squeezable tube C while pressing the downstream part of the squeezable tube C. As with the torsion spring 20 of the upstream-side holding device 17, the torsion spring 22 is attached to the swing shaft Lb and urges the holding member 21. The torsion spring 22 includes a fixed end positioned on a fixed portion of the stator 13, and a pressing end pressing the holding member 21.

The load sensor 10a serving as a displacement-detecting device is capable of detecting the radial displacement of the part of the squeezable tube C that is held by the upstream-side holding device 17. The load sensor 10a according to the first embodiment detects the load applied to the fixed end 20a of the torsion spring 20 (the urging member), thereby detecting the radial displacement of the squeezable tube C on the basis of the detected load. The load sensor 10a is capable of generating an electric signal that changes with the load applied.

Specifically, at the time of treatment, an arterial puncture needle is attached to the distal end 1aa of the arterial blood circuit 1a. Hence, when the blood is collected from the patient and is caused to flow through the arterial blood circuit 1a, a negative pressure is generated between the distal end 1aa of the arterial blood circuit 1a and the blood pump 3. When such a negative pressure is generated, the liquid pressure in the squeezable tube C decreases. Consequently, the part of the squeezable tube C that is held by the upstream-side holding device 17 is displaced in the radial direction (the diameter of that part is reduced). Therefore, the load detected by the load sensor 10a decreases. By detecting such a decrease in the load, the generation of a negative pressure in the arterial blood circuit 1a can be detected.

The load sensor 10a (the displacement-detecting device) according to the first embodiment is provided with a wiring line or the like and is thus electrically connected to the pressure-calculating device 10b. The pressure-calculating device 10b is, for example, a microcomputer or the like provided in a dialysis-apparatus body and is capable of calculating the pressure in the arterial blood circuit 1a (a liquid flow route) on the basis of the radial displacement of the squeezable tube C that is detected by the load sensor 10a (the displacement-detecting device). That is, the load sensor 10a and the pressure-calculating device 10b form the pressure-detecting device according to the present teaching. When the load sensor 10a detects any radial displacement of the squeezable tube C, a predetermined electric signal corresponding to the detected displacement is transmitted to the pressure-calculating device 10b, where the pressure (the blood-extracting pressure in the blood purification treatment) in the arterial blood circuit 1a (in the first embodiment, a portion of the arterial blood circuit 1a between the distal end 1aa and the part where the load sensor 10a is provided) is calculated.

The pressure-detecting device 10 is attached to the predetermined part of the arterial blood circuit 1a that is nearer to the distal end 1aa than the part where the blood pump 3 is provided. Therefore, the pressure-detecting device 10 can detect the suction pressure (the pressure on the suction side) of the blood pump 3. Specifically, the blood pump 3 takes in the liquid on the upstream side and discharges the liquid toward the downstream side. Hence, when the pressure (the liquid pressure) in the flow route on the upstream side changes, the suction pressure changes correspondingly. Such a pressure can be detected by the pressure-detecting device 10.

During the dialysis treatment (during the blood purification treatment), as illustrated in FIG. 5, when the blood pump 3 is activated, the rollers 15 rotate at a predetermined speed and squeeze the squeezable tube C, whereby the blood of the patient is extracorporeally circulated through the arterial blood circuit 1a and the venous blood circuit 1b. Meanwhile, the duplex pump 6 is activated. In response to this, the dialysate is supplied to the dialyzer 2 while the drain liquid is discharged, whereby the blood that is under extracorporeal circulation is purified in the dialyzer 2. To perform emergency fluid infusion or the like, the clamping device V10 is opened, whereby the dialysate is supplied through the substitution line L8 to the portion of the arterial blood circuit 1a that is on the upstream side with respect to the blood pump 3 (the distal end lea side).

The selecting device 11 is capable of selecting which of a squeezable tube C having a small diameter and a squeezable tube C having a large diameter is fitted to the blood pump 3. For example, the selecting device 11 is configured to select the squeezable tube C on the basis of information inputted at the time of setting performed before the blood purification treatment. The selecting device 11 is electrically connected to the control device 12 and is capable of transmitting, to the control device 12, information indicating whether the squeezable tube C fitted to the blood pump 3 has a small diameter or a large diameter.

The control device 12 is a microcomputer electrically connected to various devices such as actuators and sensors included in the blood purification apparatus. The control device 12 is capable of controlling the following steps in the following order a liquid-substituting step in which the tubes provided for the dialysate, such as the dialysate introduction line L1 and the dialysate drain line L2, are filled with the dialysate; a priming step in which the inside of the blood circuit 1 and the blood flow routes provided in the dialyzer 2 is substituted and filled with a priming solution (a physiological saline solution, the dialysate, or the like); a gas-purging step in which the dialysate flow routes provided in the dialyzer 2 are filled with the dialysate; a blood-removing step in which the blood of the patient is extracted into the blood circuit 1; a dialyzing step (a blood-purification-treatment step) in which the blood of the patient is purified in the dialyzer 2 while the blood is extracorporeally circulated through the blood circuit 1; a blood-returning step n which the blood in the blood circuit 1 is returned to the patient; a draining step in which the liquid in the blood circuit 1 and/or the liquid in the dialyzer 2 are/is discharged to the dialysate drain line L2; a cleaning-and-disinfecting step in which the insides of the tubes included in the dialysis apparatus are cleaned and disinfected; and a presetting step n which the operation is withheld until the subsequent liquid-substituting step is performed.

The control device 12 according to the first embodiment is electrically connected to the pressure-detecting device 10 and is capable of controlling the driving speed of the blood pump 3 in accordance with the suction pressure of the blood pump 3 that is detected by the pressure-detecting device 10. In particular, the control device 12 according to the first embodiment is capable of controlling the flow rate of the substitution fluid supplied from the substitution line L8 such that the suction pressure of the blood pump 3 that is to be detected by the pressure-detecting device 10 becomes a predetermined value. The control device 12 is also capable of controlling the driving speed of the blood pump 3 in accordance with the above suction pressure (the predetermined value) of the blood pump 3.

For example, as illustrated in FIG. 6, at the time of emergency fluid infusion in which the clamping device V10 is opened so as to allow the dialysate to be supplied from the substitution line L8, the duplex pump 6 is activated. Furthermore, the electromagnetic valves V1, V2, V4, and V7 are closed while the electromagnetic valves V3, V5, and V6 are opened. Thus, the flow rate of the substitution fluid supplied from the substitution line L8 is controlled such that the suction pressure of the blood pump 3 that is detected by the pressure-detecting device 10 becomes a predetermined value (for example, 0 mmHg).

In the above state, the driving speed (the speed of rotation of the rollers 15) of the blood pump 3 is corrected (for example, a preset number of revolutions is multiplied by a predetermined rate, a predetermined value is subtracted from or added to a preset number of revolutions, or the like). Thus, the error in the amount of discharge that is caused by the change in the suction pressure can be reduced. Furthermore, the control device 12 according to the first embodiment is capable of controlling the driving speed of the blood pump 3 in accordance with the diameter of the squeezable tube C. That is, the degree of correction of the driving speed of the blood pump 3 is changed in accordance with a characteristic regarding the amount of discharge from the squeezable tube C that is selected by the selecting device 11 (a characteristic regarding the amount of discharge from the squeezable tube C that correlates with the diameter, the thickness, or the material of the squeezable tube C). For example, if the squeezable tube C has a small diameter, the preset number of revolutions is reduced by 10%; if the squeezable tube C has a large diameter, the preset number of revolutions is reduced by 5%.

A squeezable tube C having a small diameter has a smaller thickness (is thinner) than a squeezable tube C having a large diameter. Therefore, if the suction pressure changes, the squeezable tube C having a small diameter is easier to deform, resulting in a larger error in the amount of discharge. Hence, it is preferable that the degree of reduction or increase in the driving speed of the blood pump 3 be higher in the case of a squeezable tube C having a small diameter than in the case of a squeezable tube C having a large diameter. Of course, the degree of reduction or increase in the driving speed of the blood pump 3 may be the same both in the case of a squeezable tube C having a small diameter and in the case of a squeezable tube C having a large diameter.

Now, a control process performed by the control device 12 according to the first embodiment will be described with reference to the flow chart illustrated in FIG. 7. For example, in performing substitution with the clamping device V10 being open, the duplex pump 6 is activated with the electromagnetic valves V1, V2, V4, and V7 being closed and the electromagnetic valves V3, V5, and V6 being open. Thus, the flow rate and the liquid pressure of the substitution fluid supplied to the substitution line L8 are controlled such that the suction pressure of the blood pump 3 that is detected by the pressure-detecting device 10 becomes a predetermined value (for example, 0 mmHg) (S1).

Subsequently, the driving speed (the speed of rotation of the rollers 15) of the blood pump 3 is corrected (for example, a preset number of revolutions is multiplied by a predetermined rate, a predetermined value is subtracted from a preset number of revolutions, or the like) (S2). In this step, as described above, the degree of correction of the driving speed of the blood pump 3 is changed in accordance with the diameter (small or large) of the squeezable tube C that is selected by the selecting device 11. For example, if the squeezable tube C has a small diameter, the preset number of revolutions is reduced by 10%; if the squeezable tube C has a large diameter, the preset number of revolutions is reduced by 5%.

The first embodiment employs the control device 12 that is capable of controlling the driving speed of the blood pump 3 in accordance with the suction pressure of the blood pump 3 that is detected by the pressure-detecting device 10. Therefore, the error in the amount of discharge that is caused by the change in the suction pressure of the blood pump 3 can be reduced. In particular, the first embodiment employs the substitution line L8 connected to a position of the arterial blood circuit 1*a* that is on the distal side 30 with respect to the position where the blood pump 3 is provided, and the substitution line L8 allows a predetermined substitution fluid to be supplied to the arterial blood circuit 1*a*. Furthermore, the control device 12 is capable of controlling the flow rate and the liquid pressure of the substitution fluid supplied to the substitution line L8 such that the suction pressure of the blood pump 3 that is detected by the pressure-detecting device 10 becomes a predetermined value. Therefore, the error in the amount of discharge that is caused by the change in the suction pressure of the blood pump 3 can be reduced quicker and more smoothly.

The control device 12 according to the first embodiment is also capable of controlling the driving speed of the blood pump 3 in accordance with a characteristic (the diameter) regarding the amount of discharge from the squeezable tube C. Therefore, the error in the amount of discharge that is caused by the change in the suction pressure of the blood pump 3 can be reduced more easily and more smoothly. In addition, the driving speed of the blood pump 3 can be set with consideration for the diameter of the squeezable tube C. While the first embodiment concerns a case where the driving speed of the blood pump 3 is controlled in accordance with whether the squeezable tube C has a small diameter or a large diameter, the driving speed of the blood pump 3 may be controlled in accordance with the size of the diameter of the squeezable tube C fitted to the blood pump 3.

The pressure-detecting device 10 according to the first embodiment is attached to the blood pump 3 and includes the displacement-detecting device 10*a* that detects the radial displacement of the squeezable tube C, and the pressure-calculating device 10*b* that is capable of calculating the pressure in the liquid flow route on the basis of the radial displacement of the squeezable tube C that is detected by the displacement-detecting device 10*a*. Therefore, no additional pressure-detecting device needs to be provided to an element other than the blood pump 3, providing ease of handling.

Now, results of experiments that demonstrate technical advantages of the present teaching will be described. As illustrated in FIGS. 8 and 9, for Samples 1 to 6 in which squeezable tubes C had small diameters, the suction pressure was set to 0 mmHg and the driving speed of the blood pump 3 was reduced by 10% from the preset speed, whereby the error in the amount of discharge (i.e., the flow rate) with respect to the preset flow rate was reduced overall. Furthermore, as illustrated in FIGS. 10 and 11, for Samples 1 to 6 in which squeezable tubes C had large diameters, the suction pressure was set to 0 mmHg and the driving speed of the blood pump 3 was reduced by 5% from the preset speed, whereby the error in the amount of discharge (i.e., the flow rate) with respect to the preset flow rate was reduced overall.

Furthermore, as illustrated in FIGS. 12 and 13, for Samples 1 to 6 in which squeezable tubes C had small diameters, the suction pressure was set to −150 mmHg and the driving speed of the blood pump 3 was increased by 15% from the preset speed, whereby the error in the amount of discharge (i.e., the flow rate) from the preset flow rate was reduced overall. Furthermore, as illustrated in FIGS. 14 and 15, for Samples 1 to 6 in which squeezable tubes C had large diameters, the suction pressure was set to −150 mmHg and the driving speed of the blood pump 3 was increased by 5% from the preset speed, whereby the error in the amount of discharge (i.e., the flow rate) with respect to the preset flow rate was reduced overall.

Furthermore, as illustrated in FIGS. 16 and 17, for Samples 1 to 6 in which squeezable tubes C had small diameters, the suction pressure was set to +150 mmHg and the driving speed of the blood pump 3 was reduced by 15% from the preset speed, whereby the error in the amount of discharge (i.e., the flow rate) with respect to the preset flow rate was reduced overall. Furthermore, as illustrated in FIGS. 18 and 19, for Samples 1 to 6 in which squeezable tubes C had large diameters, the suction pressure was set to +150 mmHg and the driving speed of the blood pump 3 was reduced by 10% from the preset speed, whereby the error in the amount of discharge (i.e., the flow rate) with respect to the preset flow rate was reduced overall.

Now, a second embodiment of the present teaching will be described. As with the first embodiment, a blood purification apparatus according to the second embodiment is intended for giving blood purification treatment (such as hemodialysis treatment) by extracorporeally circulating the blood of a patient and includes, as illustrated in FIG. 20, a blood circuit 1 including an arterial blood circuit 1a and a venous blood circuit 1b and that allows the blood of the patient to extracorporeally circulate therethrough; a dialyzer 2 (a blood purification device) connected to a proximal end of the arterial blood circuit 1a and to a proximal end of the venous blood circuit 1b and that purifies the blood flowing in the blood circuit 1; a blood pump 3 provided to the arterial blood circuit 1a; an arterial air-trap chamber 4 provided to the arterial blood circuit 1a; a venous air-trap chamber 5 provided to the venous blood circuit 1b; a dialysate introduction line L1 through which dialysate is introduced into the dialyzer 2; a dialysate drain line L2 through which drain liquid is discharged from the dialyzer 2; a substitution line L8; and a control device 12'. Elements that are the same as those described in the first embodiment are denoted by corresponding ones of the reference numerals, and detailed description of those elements is omitted.

The control device 12' according to the second embodiment controls the driving speed of the blood pump 3 by feeding back the suction pressure of the blood pump 3 detected by the pressure-detecting device 10. For example, if a negative pressure is detected by the pressure-detecting device 10 (that is, if the suction pressure of the blood pump 3 is negative), the amount of discharge decreases. Therefore, the driving speed of the blood pump 3 is increased. If a positive pressure is detected by the pressure-detecting device 10 (that is, if the suction pressure of the blood pump 3 is positive), the amount of discharge increases. Therefore, the driving speed of the blood pump 3 is reduced.

Now, a control process performed by the control device 12' according to the second embodiment will be described with reference to the flow chart illustrated in FIG. 21.

First, the blood pump 3 is activated and the blood is extracorporeally circulated through the blood circuit 1 (S1). Then, whether or not the suction pressure of the blood pump 3 detected by the pressure-detecting device 10 is the predetermined value (for example, 0 mmHg) is checked (S2). If it is determined that the suction pressure of the blood pump 3 is the predetermined value in step S2, the driving speed of the blood pump 3 is maintained in step S4. If it is determined that the suction pressure of the blood pump 3 is not the predetermined value in step S2, the driving speed of the blood pump 3 is corrected in step S3.

The correction of the driving speed of the blood pump 3 in the above step is performed as described above. Specifically, if a negative pressure is detected by the pressure-detecting device 10 (that is, if the suction pressure of the blood pump 3 is negative), the driving speed of the blood pump 3 is increased. If a positive pressure is detected by the pressure-detecting device 10 (that is, if the suction pressure of the blood pump 3 is positive), the driving speed of the blood pump 3 is reduced.

The second embodiment employs the control device 12' that is capable of controlling the driving speed of the blood pump 3 in accordance with the suction pressure of the blood pump 3 that is detected by the pressure-detecting device 10. Therefore, the error in the amount of discharge that is caused by the change in the suction pressure of the blood pump 3 can be reduced. In particular, the control device 12' controls the driving speed of the blood pump 3 by feeding back the suction pressure of the blood pump 3 detected by the pressure-detecting device 10. Therefore, the error in the amount of discharge that is caused by the change in the suction pressure of the blood pump 3 can be reduced more accurately.

While some embodiments have been described above, the present teaching is not limited thereto. For example, as illustrated in FIG. 22, the arterial blood circuit 1a may be provided with a first arterial air-trap chamber 4a connected to a position on the downstream side with respect to (nearer to the dialyzer 2 than) the blood pump 3, and a second arterial air-trap chamber 4b connected to a position on the upstream side with respect to (nearer to the distal end 1aa than) the blood pump 3. Furthermore, the pressure-detecting device may be a pressure sensor P3 that detects the pressure (liquid pressure) in the second arterial air-trap chamber 4b. In such a configuration, there is no need to provide a pressure-detecting device to the blood pump 3, and a blood pump for general purposes can be employed.

Alternatively, as illustrated in FIG. 23, the arterial blood circuit 1a may be provided with a substitution line L9 connected to a position nearer to the distal end 1aa than the position of the blood pump 3 and that allows a physiological saline solution (a predetermined substitution fluid) to be supplied to the arterial blood circuit 1a. The substitution line L9 is connected to a storage bag B that stores a predetermined amount of physiological saline solution. When an electromagnetic valve V11 is opened, the physiological saline solution in the storage bag B is supplied to the arterial blood circuit 1a. Note that the present teaching may be applied to an apparatus that includes neither of the substitution lines L8 and L9.

Moreover, as illustrated in FIGS. 24 and 25, a blood pump 3' may be employed that includes a stator 13, a rotor 14 rotatable on the inner side of the stator 13, rollers 15 (squeezing units) provided to the rotor 14, a pair of upper and lower guide pins 16, an upstream-side holding device 17', a downstream-side holding device 18, and a pressure transducer 10a' serving as a displacement-detecting device. Elements included in the blood pump 3' that are the same as those described in the above embodiments are denoted by corresponding ones of the reference numerals, and detailed description of those elements is omitted.

The upstream-side holding device 17' is provided for holding the upstream side (a part where the arterial blood circuit 1a of the distal end 1aa side is connected) of the squeezable tube C fitted in the fitting recess 13a of the stator 13 of the blood pump 3'. As illustrated in FIG. 25, the upstream-side holding device 17 includes a holding member 19 capable of holding the squeezable tube C while pressing the squeezable tube C in the radial direction, and a torsion spring 20 (an urging member) urging the holding member 19 toward the squeezable tube C.

The pressure transducer 10a' serving as a displacement-detecting device is capable of detecting the radial displacement of the part of the squeezable tube C that is held by the upstream-side holding device 17'. The pressure transducer 10a' according to the present embodiment is provided at a position across the squeezable tube C from the holding member 19. The pressure transducer 10a' detects the pressure applied to the peripheral side face of the squeezable tube C pressed by the holding member 19, thereby detecting the radial displacement of the squeezable tube C on the basis of the detected pressure.

Specifically, if a negative pressure is generated between the distal end 1aa of the arterial blood circuit 1a and the blood pump 3' when the blood is collected from the patient and is caused to flow through the arterial blood circuit 1a, the liquid pressure in the squeezable tube C decreases, and the part of the squeezable tube C that is held by the upstream-side holding device 17' tends to be displaced in the radial direction (the diameter of that part tends to be reduced). Therefore, the area of contact of the squeezable tube C with the pressure transducer 10a' is reduced, and the pressure detected by the pressure transducer 10a' is reduced correspondingly. By detecting such a reduction in the pressure, the generation of a negative pressure in the arterial blood circuit 1a can be detected.

As with the first embodiment, the pressure transducer 10a' (the displacement-detecting device) according to the present embodiment is provided with a wiring line or the like and is thus electrically connected to the pressure-calculating device 10b. The pressure-calculating device 10b is, for example, a microcomputer or the like provided in a dialysis-apparatus body and is capable of calculating the pressure in the arterial blood circuit 1a (a liquid flow route) on the basis of the radial displacement of the squeezable tube C that is detected by the pressure transducer 10a' (the displacement-detecting device). That is, the pressure transducer 10a' (the displacement-detecting device) and the pressure-calculating device 10b form the pressure-detecting device according to the present teaching.

Furthermore, as with the above embodiments, the suction pressure of the blood pump 3' is detectable by the pressure transducer 10a' (the displacement-detecting device) and the pressure-calculating device 10b that form the pressure-detecting device. As described above, the holding device (the upstream-side holding device 17') includes the holding member 19 capable of holding the squeezable tube C while pressing the squeezable tube C in the radial direction, and the torsion spring 20 (the urging member) urging the holding member 19 toward the squeezable tube C. Furthermore, the displacement-detecting device is provided at a position across the squeezable tube C from the holding member 19 and detects the pressure applied to the peripheral side face of the squeezable tube C pressed by the holding member 19, thereby detecting the radial displacement of the squeezable tube C on the basis of the detected pressure. Therefore, the displacement-detecting device provided to the blood pump 3' can have a function of receiving a pressing force applied to the squeezable tube C and a function of detecting the pressure in the liquid flow route at a position of the arterial blood circuit 1a that is nearer to the distal end 1aa than the blood pump 3.

The present teaching is applicable to any blood purification apparatus having a different appearance, any additional functions, or the like, as long as the apparatus includes a control device that is capable of controlling the driving speed of a blood pump in accordance with the suction pressure of the blood pump that is detected by a pressure-detecting device.

REFERENCE SIGN LIST 1 blood circuit (liquid flow route)
1a arterial blood circuit
1b venous blood circuit
2 dialyzer (blood purification device)
3, 3' blood pump (peristaltic pump)
4 arterial air-trap chamber
5 venous air-trap chamber
6 duplex pump
7 ultrafiltration pump
8 pressurizing pump
9 degassing chamber
10 pressure-detecting device
11 selecting device
12, 12' control device
13 stator
14 rotor
15 roller (squeezing unit)
16 guide pin
17, 17' upstream-side holding device
18 downstream-side holding device
19 holding member
20 torsion spring (urging member)
21 holding member
22 torsion spring
C squeezable tube

The invention claimed is:
1. A blood purification apparatus that includes:
a blood circuit including an arterial blood circuit and a venous blood circuit to distal ends of which puncture needles are connectable, respectively, and through which blood of a patient is extracorporeally circulated;
a blood purification device connected to proximal ends of the arterial blood circuit and the venous blood circuit and that purifies the blood extracorporeally circulating through the blood circuit;
a squeezable tube connected to the arterial blood circuit;
a blood pump allowing liquid in the squeezable tube to flow by squeezing the squeezable tube in a lengthwise direction while compressing the squeezable tube in a radial direction;
a pressure-detecting device located on a suction side of the blood pump, and the pressure-detecting device is attached to a predetermined position of the arterial blood circuit that is on a distal side with respect to a position where the blood pump is provided so that the pressure-detecting device is capable of detecting a suction pressure of the blood pump, and a substitution line connected to a position of the arterial blood circuit that is on the distal side with respect to the position where the blood pump is provided, the substitution line allowing a predetermined substitution fluid to be supplied to the arterial blood circuit;

the blood purification apparatus further comprising:

a control device controlling a driving speed of the blood pump based upon a measurement of the suction pressure of the blood pump that is detected by the pressure-detecting device, wherein the control device controls a flow rate of the predetermined substitution fluid supplied from the substitution line such that the suction pressure of the blood pump becomes a predetermined value during a dialysis treatment when the puncture needles are connected to the patient.

2. The blood purification apparatus according to claim 1, wherein the control device is capable of controlling the driving speed of the blood pump in accordance with a characteristic regarding an amount of discharge from the squeezable tube.

3. The blood purification apparatus according to claim 1, wherein the control device controls the driving speed of the blood pump by feeding back the suction pressure of the blood pump that is detected by the pressure-detecting device.

4. The blood purification apparatus according to claim 1, wherein the pressure-detecting device is attached to the blood pump and includes:

a displacement-detecting device that detects a radial displacement of the squeezable tube; and a pressure-calculating device that is capable of calculating a pressure in a liquid flow route in accordance with the radial displacement of the squeezable tube that is detected by the displacement-detecting device.

5. The blood purification apparatus according to claim 1, wherein a bubble-detecting device is located on the arterial blood circuit between the distal end of the arterial blood circuit and the substitution line.

6. The blood purification apparatus according to claim 5, wherein the bubble-detecting device includes an ultrasonic receiving element formed of a piezoelectric element.

7. The blood purification apparatus according to claim 1, wherein the driving speed of the blood pump is maintained or changed based upon a difference in the suction pressure of the blood pump relative to the predetermined value.

8. The blood purification apparatus according to claim 1, wherein the blood circuit further includes a dialyzer in the venous blood circuit.

9. The blood purification apparatus according to claim 8, wherein an air-trap chamber is located upstream of the dialyzer and an air-trap chamber is located downstream of the dialyzer.

10. The blood purification apparatus according to claim 9, wherein the air-trap chamber located upstream is located directly upstream of the dialyzer so that blood moves from the air-trap chamber located upstream into the dialyzer.

11. The blood purification apparatus according to claim 9, wherein the air-trap chamber located downstream is located directly downstream of the dialyzer so that blood from the dialyzer extends into the air-trap chamber downstream.

12. The blood purification apparatus according to claim 1, wherein a first end of the substitution line is connected to the arterial blood circuit on the suction side of the blood pump so that the substitution fluid is configured to be provided to the arterial blood circuit and a second end of the substitution line is connected to a sampling port in a dialysate introduction line, and wherein the substitution fluid extends from the dialysate introduction line to the arterial blood circuit through the substitution line.

13. The blood purification apparatus according to claim 12, wherein the substitution line includes a clamping device that is openable and closable to supply the substitution fluid to the blood circuit.

14. The blood purification apparatus according to claim 1, wherein a second arterial air-trap chamber is located between the substitution line and the suction side of the blood pump.

15. The blood purification apparatus according to claim 14, wherein the second arterial air-trap chamber includes a pressure sensor that detects pressure in the second arterial air-trap chamber.

16. The blood purification apparatus according to claim 1, wherein the driving speed of the blood pump is corrected in accordance with a characteristic regarding an amount of discharge from the squeezable tube that is selected by a selecting device is configured to select a type of the squeezable tube that is fitted into the blood pump, and wherein characteristics of the squeezable tube correlate with a diameter, thickness, or material of the squeezable tube.

17. A blood purification apparatus that includes:

a blood circuit including an arterial blood circuit and a venous blood circuit to distal ends of which puncture needles are connectable, respectively, and through which blood of a patient is extracorporeally circulated;

a blood purification device connected to proximal ends of the arterial blood circuit and the venous blood circuit and that purifies the blood extracorporeally circulating through the blood circuit;

a squeezable tube connected to the arterial blood circuit;

a blood pump allowing liquid in the squeezable tube to flow by squeezing the squeezable tube in a lengthwise direction while compressing the squeezable tube in a radial direction;

a pressure-detecting device located on a suction side of the blood pump, and the pressure-detecting device is attached to a predetermined position of the arterial blood circuit that is on a distal side with respect to a position where the blood pump is provided so that the pressure-detecting device is capable of detecting a suction pressure of the blood pump, and a substitution line connected to a position of the arterial blood circuit that is on the distal side with respect to the position where the blood pump is provided, the substitution line allowing a predetermined substitution fluid to be supplied to the arterial blood circuit;

the blood purification apparatus further comprising:

a control device controlling a driving speed of the blood pump based upon a measurement of the suction pressure of the blood pump that is detected by the pressure-detecting device, wherein the control device controls a flow rate of the predetermined substitution fluid supplied from the substitution line such that the suction pressure of the blood pump becomes a predetermined value and wherein the blood purification apparatus further includes a selecting device that is configured to select a type of the squeezable tube that is fitted into the blood pump, and characteristics of the squeezable tube correlate with a diameter, thickness, or material of the squeezable tube.

18. The blood purification apparatus according to claim 17, wherein the selecting device elects the type of the squeezable tube on a basis of information inputted at a time before blood purification treatment.

19. The blood purification apparatus according to claim 17, wherein the selecting device is electrically connected to the control device and is capable of transmitting information about the squeezable tube in the blood pump to the control device.

20. The blood purification apparatus according to claim 19, wherein the information about the squeezable tube is whether the squeezable tube has a small diameter or a large diameter.

* * * * *